(12) United States Patent
Dove

(10) Patent No.: US 7,943,003 B2
(45) Date of Patent: May 17, 2011

(54) LOW STRESS TO SEAL EXPANDED PTFE GASKET TAPE

(75) Inventor: Kevin E. Dove, Wilmington, DE (US)

(73) Assignee: Gore Enterprise Holdings, Inc., Newark, DE (US)

( * ) Notice: Subject to any disclaimer, the term of this patent is extended or adjusted under 35 U.S.C. 154(b) by 787 days.

(21) Appl. No.: 11/620,397

(22) Filed: Jan. 5, 2007

(65) Prior Publication Data

US 2007/0102114 A1  May 10, 2007

Related U.S. Application Data

(62) Division of application No. 10/798,917, filed on Mar. 10, 2004, now Pat. No. 7,179,525.

(51) Int. Cl.
*B32B 37/00* (2006.01)
*B29C 65/00* (2006.01)

(52) U.S. Cl. .................... 156/308.2; 156/324

(58) Field of Classification Search .......... 156/308.2, 156/309.6, 324; 428/316.6; 277/627, 654
See application file for complete search history.

(56) References Cited

U.S. PATENT DOCUMENTS

| | | | |
|---|---|---|---|
| 3,953,566 A | 4/1976 | Gore | 264/288 |
| 4,096,227 A | 6/1978 | Gore | 264/210 |
| 4,187,390 A | 2/1980 | Gore | 174/102 |
| 4,985,296 A | 1/1991 | Mortimer, Jr. | 428/220 |
| 4,990,296 A | 2/1991 | Pitolaj | 264/162 |
| 5,486,010 A | 1/1996 | Hamilton et al. | 277/312 |
| 5,492,336 A | 2/1996 | Barna et al. | 277/314 |
| 5,964,465 A | 10/1999 | Mills et al. | 277/316 |
| 5,992,857 A | 11/1999 | Ueda et al. | 277/592 |
| 6,485,809 B1 | 11/2002 | Minor et al. | 428/66.4 |
| 2003/0003290 A1 | 1/2003 | Hisano et al. | 428/308.4 |
| 2003/0230859 A1 | 12/2003 | Hisano et al. | 277/610 |
| 2004/0232624 A1 | 11/2004 | Hisano et al. | 277/500 |
| 2005/0225037 A1 | 10/2005 | Dove | 277/610 |

FOREIGN PATENT DOCUMENTS

| | | |
|---|---|---|
| DE | 20200636 | 3/2002 |
| DE | 20204054 | 5/2002 |
| JP | 2002/243041 | 8/2002 |
| JP | 2004/003617 | 1/2004 |
| WO | 01/27501 | 4/2001 |

OTHER PUBLICATIONS

"Unit Cell Information on Some Important Polymers", Physical Properties of Polymers Handbook, Chapter 30, American Insitute of Physics, 1996.

*Primary Examiner* — John L Goff
(74) *Attorney, Agent, or Firm* — Carol A. Lewis White

(57) ABSTRACT

A low stress to seal, unitary gasket tape is provided that is particularly suited for use in form-in-place gaskets. The gasket tape preferably comprises at least two joined porous expanded polytetrafluoroethylene (ePTFE) tapes aligned along tape side surfaces and a substantially air impermeable layer there between. The plane of expansion of the ePTFE is substantially parallel to the flange surface providing longitudinal and transverse strength. The substantially air impermeable layer prevents fluid from permeating through the gasket in the radial direction.

25 Claims, 14 Drawing Sheets

LOW STRESS TO SEAL EXPANDED PTFE GASKET TAPE

RELATED APPLICATIONS

This application is a divisional application of commonly owned U.S. patent application Ser. No. 10/798,917 filed on Mar. 10, 2004, now U.S. Pat. No. 7,179,525.

BACKGROUND OF THE INVENTION

A wide variety of gaskets are known for use in sealing applications. Porous expanded polytetrafluoroethylene (PTFE) is widely used today as a gasket material. As disclosed in U.S. Pat. No. 3,953,566 to Gore, this material has numerous properties making it highly desirable as a gasket. These properties include being readily compressible and conformable, being chemically resistant, having relatively high strength, and being far less prone to creep relaxation and loss of sealing pressure than non-expanded, non-porous PTFE alone.

Furthermore, gaskets made from biaxially or multiaxially expanded PTFE have improved sealing performance as compared to uniaxially expanded PTFE gaskets. For example, gaskets made from multiaxially expanded PTFE are resistant to creep relaxation and cold flow in multiple directions. The multi-directional tensile strength in multiaxially expanded PTFE gaskets provides circumferential and radial strength to the gasket and increases the cut through resistance of the gasket. Enhanced radial strength and cut through resistance provided by multiaxially expanded PTFE is achieved when the plane of expansion of the expanded PTFE is substantially parallel to the flange surface on which the gasket is installed.

In many sealing applications, the gasket is used to seal the junction between flanges, such as between pipes. In such applications, expanded PTFE is a desirable material for the gaskets because the expanded PTFE gasket can be placed between the flanges, and the flanges can then be pressed together with the application of force, such as by tightening of bolts. This application of force compresses the expanded PTFE. As the expanded PTFE is compressed, its initial pore volume is reduced, thus densifying the expanded PTFE. Particularly with metal-to-metal flanges, it is possible to apply sufficient force (or "stress") to the flanges to fully densify the expanded PTFE. Thus, in at least part of the expanded PTFE gasket, the pore volume is reduced to substantially zero, such that a fluid contained within the pipes is prevented from leaking between the flanges by the densified, non-porous PTFE gasket, which seals the flanges.

In many applications, particularly when harsh chemicals are used which could readily break down the metal, or the metal could contaminate the chemical which is being transported or housed, it is common to use glass-lined steel, glass, or fiberglass reinforced plastic ("FRP") piping and vessels. Because this equipment is often used with extremely harsh chemicals, there is great desire to use PTFE gaskets to seal the connecting flanges of this equipment because of the well known extraordinary chemical resistance of PTFE. Unfortunately, non-expanded, non-porous PTFE gaskets are generally not conformable enough to effectively seal this type of equipment. In the case of glass-lined steel flanges, although there is a relatively smooth finish, there is often a large amount of unevenness or lack of flatness associated with the flanges. This unevenness or lack of flatness requires the gasket to conform to large variations around the perimeter as well as between the internal and external diameter of the flange in order for an effective seal to be created. Thus, a non-expanded, non-porous PTFE gasket is not conformable enough to provide an adequate seal in many of these applications.

Because expanded PTFE is conformable, it would be desirable to use expanded PTFE to seal these commonly uneven flanges. Unfortunately, in many applications it is not possible to apply sufficient force to the flanges to create enough gasket stress to fully densify the expanded PTFE gasket to create an effective seal. For example, glass-lined steel piping flanges, glass flanges, or FRP piping flanges may deform, fracture, or break upon the application of a high amount of stress. Thus, in these applications, an expanded PTFE gasket may not be completely densified to reach a non-porous state, and therefore does not become leak proof, because the maximum stress that can be applied to the flanges without breaking them is not sufficient to densify the gasket. In some constructions where expanded PTFE gasket is not densified to a substantially non-porous state, leakage can occur through the residual porosity within the gasket. Often, this leakage is detected immediately after the installation of the gasket through either a "sniffing" technique or a "bubble test". In the bubble test, a solution such as soapy water is applied to the gasketed flange and an internal air pressure is applied to the piping system or vessel. If a leak of a sufficient rate is present, bubbles will form in the soapy water solution. In some cases, a leak may exist but a rate small enough not to form a bubble. Where corrosive chemicals are being processed, the leak may persist for months or years and the corrosive chemicals can eventually leak through the gasket and attack the flange bolts or clamps resulting in a catastrophic failure of the flange.

U.S. Pat. No. 6,485,809, in the name of Minor et al., teaches a low stress to seal gasket construction comprising a multilayer, unitary gasket including at least one inner layer of expanded PTFE disposed between a first and second substantially air impermeable outer layer, and a substantially air impermeable region bridging the first and second substantially air impermeable layers. By "low stress to seal" is meant a gasket which provides a substantially air tight, or air impermeable, seal upon the application of a relatively low stress (i.e., a stress below that required to fully densify a porous expanded PTFE gasket, generally less than about 20,700 kPa (3000 psi)). This patent teaches gaskets which are stamped or cut from multilayered laminated sheets formed by wrapping layers around a mandrel, and subjecting gaskets to compressive treatment to compress a discreet portion and form an air impermeable region. While this patented construction may overcome many challenges in creating a low stress to seal gasket, there are limitations to the sizes of gaskets that can be produced when cutting gaskets from sheet goods. The largest size gasket that can be produced when cutting from sheet gasketing cannot be larger than the sheet size itself. Another concern with the manufacturing of such large size gaskets from sheet gasketing materials is the cost associated with producing such gaskets. For example, tooling costs for large size gaskets can be quite expensive and the manufacturing efficiencies of cutting gaskets from sheet stock can be relatively low especially with large diameter gaskets. When cutting gaskets from sheet stock, it is not uncommon to experience a sheet utilization yield of only 40% where the remaining 60% of the sheet is scrapped due to center drops, poor nesting of different size gaskets and unused corner sections.

U.S. Pat. No. 4,990,296 to Pitolaj teaches a method of welding together filled sintered PTFE components, wherein large diameter gaskets can be formed in sections by welding the ends of the sections together. This method, while perhaps suitable for sintered filled PTFE, would not be suitable for soft, porous expanded PTFE which would densify as a result of the applied heat and pressure at the welded joint. Densification would result in thinner, hard and non-conformable sections within the gasket which would less effectively seal fragile flanges such as glass lined steel and FRP flanges.

U.S. Pat. No. 5,964,465 to Mills et al. teaches a biaxially expanded PTFE form-in-place type gasket that is ideally suited for large size flanges. Form-in-place gaskets have the advantage of being able to be formed to any size flange without the limitations of gaskets cut from sheet stock such as low material utilization rates and expensive tooling costs. Form-in-place gaskets made in accordance with the teachings of Mills et al., comprised of biaxially expanded PTFE, may have additional advantages offered by the biaxially expanded PTFE such as chemical resistance, dimensional stability, and resistance to creep relaxation. However, as previously noted, since adequate gasket stress cannot be applied to densify the ePTFE, these gaskets cannot effectively seal glass lined steel and FRP flanges.

In PCT publication WO01/27501 A1 to Dove et al., a form-in-place gasket comprising an inner layer of expanded PTFE and substantially air impermeable outer layers that are bridged by a substantially impermeable region is taught. The substantially air impermeable outer layers and substantially air impermeable region are intended to prevent permeation through the expanded PTFE gasket material. The purpose of this gasket construction is to provide a tight seal at the low stresses where ePTFE alone can not be fully densified by preventing leakage through the porous ePTFE. However, gaskets constructed according to the teachings of WO 01/27501 are subject to a number of disadvantages. For example, outer air impermeable layers made of incompressible materials such as full density PTFE or densified expanded PTFE may increase the stiffness of the gasket, making it too rigid for a form-in-place gasket. It is desirable for form-in-place gaskets to be flexible so that they can be formed to the geometry of the flange.

Further, form-in-place gaskets comprising biaxially expanded PTFE are typically joined at the ends by skive-cutting the ends on a diagonal and overlapping the skive cut ends as taught in U.S. Pat. No. 5,964,465. Form-in-place gaskets constructed in accordance with PCT publication WO01/27501 A1 to Dove et al. having the outer impermeable layers, cannot be joined by overlapping the ends of the tape using the skive cutting technique without compromising the air impermeable nature of the material. When a skive cut is made through the outer air impermeable layers, porous expanded PTFE is exposed, providing a leak path through the gasket.

In U.S. Patent Publication No. 2003/0003290 A1 to Hisano et al., a sealing material in the form of a tape is taught which consists of laminated layers of porous expanded PTFE which are slit into strips having a height greater than the width, and wherein the laminated end faces on the long side of the laminated strip are in contact with the tightening surface. A plurality of the laminated strips may be joined together on the laminated surfaces of the laminate with tetrafluoroethylene-hexafluoropropylene copolymer or tetrafluoroethylene-perfluoroalkyl vinyl ether copolymer film. It is further taught that at least one layer may be interposed within the laminate for preventing fluid penetration. In the form of a closed ring or gasket where the longitudinal beginning and end of the tape has been joined, the layers of expanded PTFE and the layer for preventing fluid penetration are vertically oriented when the gasket is installed on a flange surface. The layers intended to prevent fluid penetration in the radial direction may provide the gasket with low stress to seal capability by preventing leakage through the porous ePTFE. For gaskets made according to this method, the longitudinal strength of the expanded PTFE provides strength to the gasket in the circumferential direction when the gasket is installed on a flange surface. However, with the ePTFE layers laminated in the width direction, the transverse directional strength of the ePTFE is oriented in the vertical or "z" direction of the gasket. Therefore, little to no strength is provided to the gasket in the radial direction. Therefore, gaskets taught in U.S. Patent Publication No. 2003/0003290 A1 would be prone to cold flow in the width direction and lack dimensional stability. For gasketing applications involving glass lined steel flanges it is critical for the gasket material to be dimensionally stable to prevent fracture of the glass lining.

It would be desirable to provide a unitary, chemically resistant, dimensionally stable, high strength gasket material that can seal openings, especially glass-lined steel and FRP flanges, upon the application of a relatively low stress. Preferred gaskets made from this material are form-in-place gaskets, and it is further desirable that such a gasket can be installed using the common skive cutting techniques for overlapping the ends of the tape. Accordingly, it is the purpose of the present invention to provide an expanded PTFE tape that when in the form of a gasket provides a substantially air impermeable seal upon the application of a low stress, that is dimensionally stable and can be installed using the skive cutting overlap method.

SUMMARY OF THE INVENTION

The present invention is directed to a novel composite tape suitable for use as a gasket, particularly form-in-place gaskets, that provides a substantially air impermeable seal with low load upon the tightening surfaces, and with low stress applied to the gaskets. Gaskets formed from the composite tape of the present invention exhibit excellent dimensional stability and resistance to creep relaxation in both the longitudinal and transverse direction.

Preferred gaskets are formed from composite tape comprising at least two laminated multilayered porous expanded PTFE tapes having upper and lower laminate layers, and side surfaces which extend between the upper and lower laminate layers. The composite tape further comprises at least one substantially air impermeable layer positioned between the side surfaces of the at least two tapes. The porous ePTFE tapes are formed from multilayer tape or monolithic ePTFE, wherein the plane of expansion of the ePTFE is in the x-y plane of the tape. Where the tape comprise ePTFE layers, upper and lower tape layers of the tape are parallel to the plane of expansion. Where the ePTFE tape is monolithic, the plane of expansion of the ePTFE is parallel to the x-y plane of the tape. Preferred are composite tapes wherein the at least two ePTFE tapes are bonded along side surfaces by a substantially air impermeable layer comprising a melt processable fluoropolymer. Gaskets formed from composite tape of the present invention have upper and lower gasket surfaces substantially parallel to the plane of expansion of the ePTFE, and substantially parallel to the x-y plane of the tape. The plane of expansion of ePTFE can be determined, for example, by Wide-Angle X-ray Scattering test methods, as described herein.

The present invention is further directed to novel methods for forming the composite tape of the present invention. Methods comprise bonding together multiple tapes, such as multilayered porous expanded PTFE tapes, along laminated side surfaces and providing a substantially air impermeable layer between the tapes. Preferred methods comprise first bonding a substantially air impermeable layer onto tape side surfaces prior to joining at least two tapes to form a composite.

Gaskets made from composite tapes of the present invention had significantly lower leak rates than comparative examples (e.g. FIGS. 2 and 3 ) when tested for sealability. A decrease in leak rate of at least about two orders of magnitude was realized with gaskets formed from the inventive materials having an impermeable layer as compared with gaskets formed from ePTFE tape without any impermeable layers interposed therein. When compared with gaskets having ePTFE layers laminated in the width direction and fluid penetration preventing layers comprising densified ePTFE, a reduction in leak rate of at least about one order of magnitude was realized with the inventive materials. The reduction in leak rate of gaskets formed from composite tape of the present invention is attributable in part to the substantially parallel orientation of the plane of expansion of the expanded PTFE with the flange surface and the incorporation of substantially air impermeable layers between joined tapes.

Tensile Strength tests illustrate that the bond strength of the welded joint of the composite tape of the present invention is significantly stronger than the bond strength of other laminated tape. Gasket materials formed from ePTFE film layers laminated perpendicular to the x-y plane of the gasket demonstrate reduced the tensile strength in the width direction compared to the inventive materials. Furthermore, the amount of extension in the inventive materials at maximum stress was significantly less compared to the extension of other materials. The results indicate that gasket materials of the present invention, when compressed between flanges, will be less likely to cold flow.

BRIEF DESCRIPTION OF THE DRAWINGS

A fuller understanding of the present invention will be gained by reference to the following detailed description when read in conjunction with accompanying drawings. It should be understood that the invention is not limited to the precise arrangement shown.

DETAILED DESCRIPTION OF THE INVENTION

The present invention is directed to a novel sealing material in the form of a composite tape suitable for use as a gasket, including form-in-place gaskets. Gaskets formed from this material provide a substantially air impermeable seal with low load upon the tightening surfaces, and with low stress applied to the gaskets. Gaskets of the present invention exhibit excellent dimensional stability and resistance to creep relaxation in both the longitudinal and transverse direction. The present invention is further directed to novel methods for forming novel composite tape of the present invention. Methods are disclosed for bonding together multiple tapes, such as multilayered porous expanded PTFE tapes, along laminated side surfaces and providing a substantially air impermeable layer between the tapes. The novel methods provide sealing material for making low stress to seal gaskets, preferably low stress to seal form-in-place gaskets, having low creep relaxation.

As previously stated, by "low stress to seal" is meant a gasket which provides a substantially air tight, or air impermeable, seal upon the application of a relatively low stress (i.e., a stress below that required to fully densify a porous expanded polytetrafluoroethylene (ePTFE) gasket, generally less than about 20,700 kPa (3000 psi)).

By "air impermeable" as used herein is meant resistant to the transport of air through a material. Permeability may be measured using any known techique, such as ASTM D-1434-82 (2003).

By "form-in-place" is meant a gasket that is reshaped or formed to correspond to the sealing surface during the application of the gasket. Typical form-in-place gaskets are made from material provided as a narrow, flexible, continuous strip of material (i.e. tape) or cord to be cut and shaped to the dimensions of the sealing surface. For example, a form-in-place gasket suitable for use with a glass-lined flange of a vessel, may be provided as a flexible tape to be bent into a shape matching the perimeter of the flange. Adhesives are typically used to hold the gasket against the flange until a mating flange is secured compressing the gasket between the two flanges.

Figure 1:
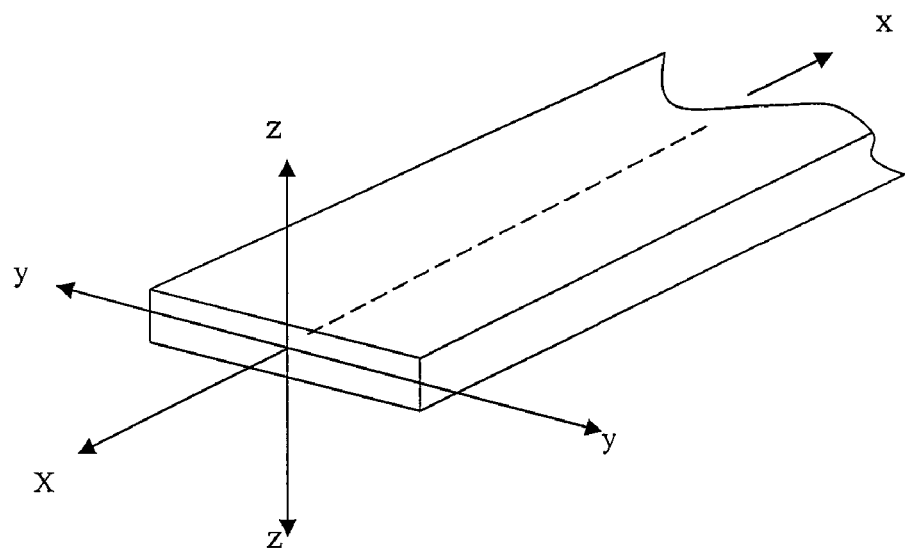
FIG. 1 is a three-quarter perspective view of a conventional gasketing tape and orientation.
Figure 4:
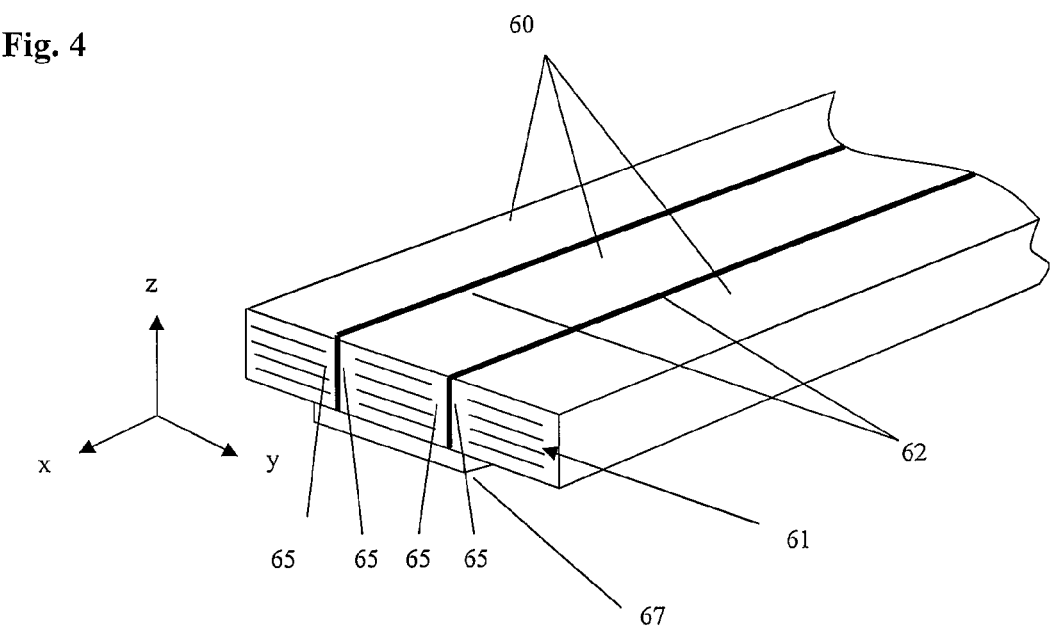
FIG. 4 is a three-quarter perspective view of a composite low stress to seal tape of the present invention comprising barrier layers and an adhesive layer.
Figure 5:
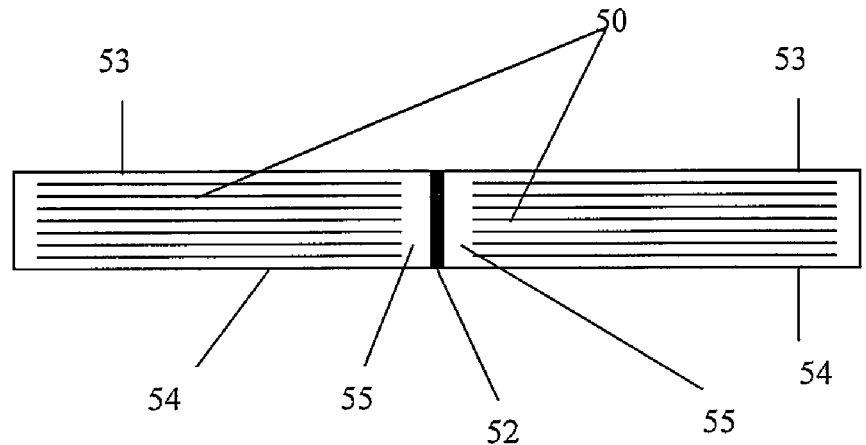
FIG. 5 is a cross-sectional view of a composite low stress to seal tape of the present invention having one barrier layer.
Figure 6:
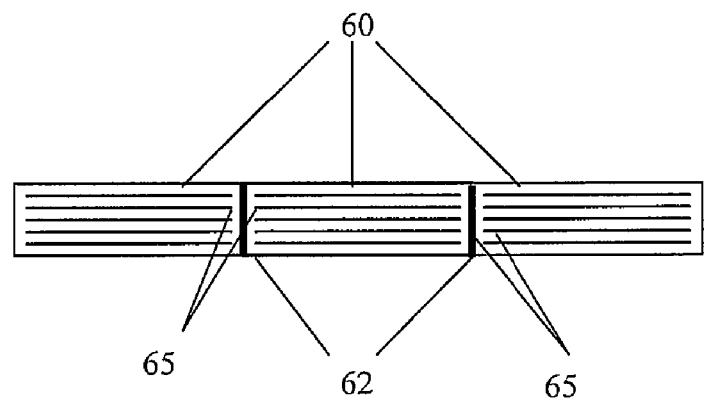
FIG. 6 is a cross-sectional view of a composite low stress to seal tape of the present invention having two barrier layers.

Shown in FIG. 1 is a conventional gasketing element constructed from longitudinally expanded polytetrafluoroethylene (ePTFE) material. As previously explained herein, due to the tendency of longitudinally expanded PTFE to creep when formed as a gasket and placed under compressive pressure in the "z" direction (thickness direction), the material tends to spread in the "y" direction (transverse direction) and to a lesser degree in the longitudinal "x" direction. Exemplary embodiments of the present invention are illustrated in FIGS. 4, 5 and 6. Shown in FIG. 5, is a cross-section of a gasket formed from composite tape comprising two laminated multilayered porous expanded PTFE tapes 50 having upper and lower laminate layers 53 and 54 and side surfaces 55 which extend between the upper and lower laminate layers. A substantially air impermeable layer 52 is between the side surfaces 55 of the two tapes 50.

Porous ePTFE tapes suitable for use in the present invention are formed from multilayer tape wherein the plane of expansion of the ePTFE is in the x-y plane of the tape, and the ePTFE layers, including upper and lower tape layers of the tape, are parallel to the plane of expansion. Where the ePTFE tape is monolithic, the plane of expansion of the ePTFE is parallel to the x-y plane of the tape. At least two ePTFE tapes are joined together, aligned along side surfaces, wherein the tape side surfaces extend between upper and lower tape layers or tape surfaces. The at least two tapes are joined to form a composite tape wherein the plane of expansion of the ePTFE within the composite tape is the x-y plane of the composite tape. Gaskets formed from composite tape of the present invention have upper and lower gasket surfaces substantially parallel to the plane of expansion of the ePTFE, and substantially parallel to the x-y plane of the tape. The plane of expansion of ePTFE can be determined, for example, by Wide-Angle X-ray Scattering test methods, as described herein.

FIGS. 4 and 6 illustrate a gasket formed from composite tape comprising three multilayered laminate porous PTFE tapes 60 and two substantially air impermeable layers 62 positioned between the porous PTFE tape side surfaces 65.

Figure 8:
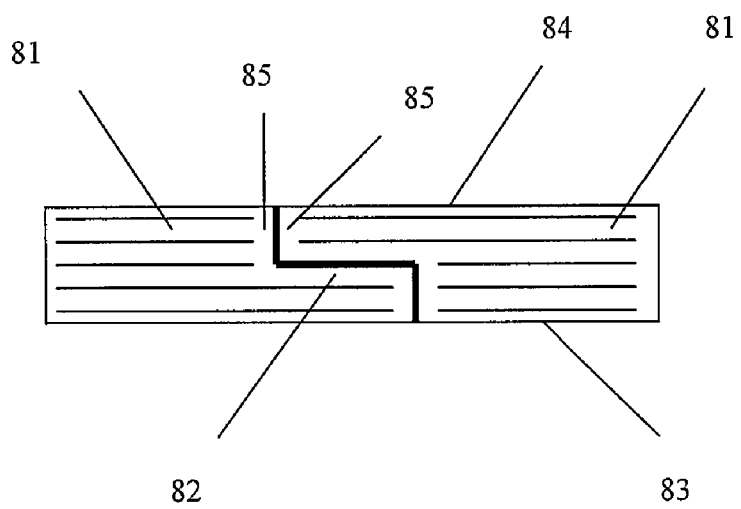
FIG. 8 is a cross-sectional view of a composite low stress to seal tape of the present invention having one barrier layer.
Figure 9:
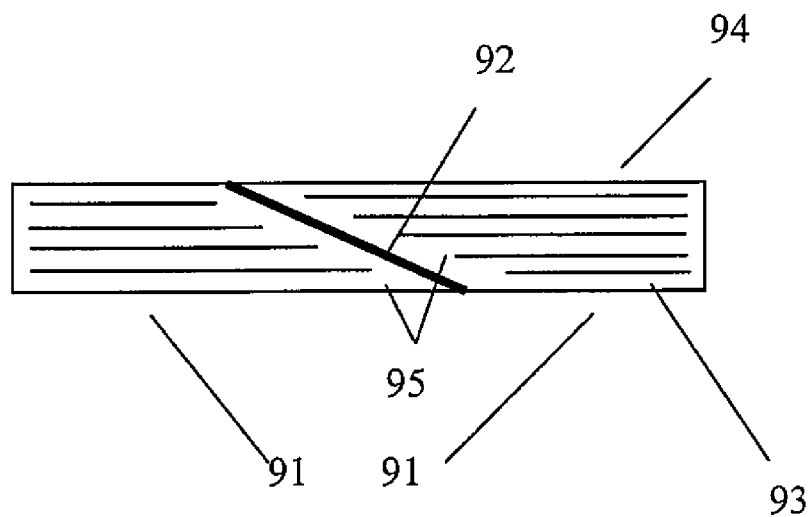
FIG. 9 is a cross-sectional view of a composite low stress to seal tape of the present invention having an angled barrier layer.

In many embodiments of the present invention, the substantially air impermeable layer is positioned between tape side surfaces perpendicularly to the upper and lower tape and gasket surfaces. However, FIGS. 8 and 9 illustrate embodiments of the present invention wherein tape side surfaces extending between upper and lower laminate layers are not completely perpendicular to the upper and lower laminate layers. FIG. 8 illustrates a gasket formed from a composite tape comprising two tapes 81 joined by a substantially air impermeable material 82 in which tape side surfaces 85 extending between upper and lower laminate layers 83 and 84 are stepped. FIG. 9 illustrates a gasket formed from a composite tape comprising two joined tapes 93 and a substantially air impermeable material 92 in which tape side surfaces 95 extending between upper and lower laminate layers 93 and 94 are angled.

Composite tape of the present invention is formed from at least two tapes, each comprising porous expanded PTFE, which are aligned along tape side surfaces. Composite tapes of the present invention may be formed from at least two tapes, at least three tapes, or a plurality of tapes, and is not particularly limited by the number of tapes which may be joined to form the composite. Composite tape further comprises at least one substantially air impermeable layer between aligned side surfaces of the at least two tapes to be joined. As previously stated, each tape making up the composite may be monolithic or multilayered porous expanded PTFE. Preferred porous expanded PTFE comprises microporous expanded PTFE as taught in U.S. Pat. Nos. 3,953,566 and 4,187,390, incorporated herein by reference. PTFE may be expanded uniaxially, biaxially, or multiaxially, and preferably has a density of less than 1.8 g/cc, more preferred less than 1.2 g/cc, further preferred less than 1.0 g/cc, and a most preferred density of less than 0.8 g/cc. While not limited by a number of porous expanded PTFE layers, preferred multilayered tape is formed from multiple self-adhered porous expanded PTFE layers, made by any method known in the art for forming multilayered porous expanded PTFE tapes; methods suitable for use in the present invention are described, for example, in U.S. Pat. No. 5,964,465, and 6,485,809 which are hereby incorporated herein by reference. Suitable tape for use in making composite tape of the present invention is commercially available, for example, under the trade names GORE-TEX® Gasket Tape, GORE-TEX® Series 300 Gasket Tape and GORE-TEX® Series 600 Gasket Tape (W.L. Gore & Assoc., Inc., Elkton, Md.).

While preferably the multilayer ePTFE tape used to form the composite tape consists essentially of a plurality of ePTFE layers, alternately, one or more tape layers may comprise materials other than a PTFE material to provide desired properties to the gasket. For example, one or more of polymeric films; metal foils, metal screens or the like may be provided to the multilayered tape to enhance properties to the resulting gasket. In a preferred embodiment a composite tape is formed from at least two multilayered laminated ePTFE tapes in which upper and lower laminate layers are ePTFE.

At least a portion of the porous expanded PTFE, or at least one layer of multilayered PTFE tape, may be coated or filled to provide desired properties to the gasket. For example, expanded PTFE may be coated to provide properties such as resilience, electrochemical responsiveness, added strength, further reduced creep relaxation, and the like. Additionally, porous expanded PTFE may be filled with various fillers, for example, such as those used to fill expanded microporous PTFE sheets as taught in U.S. Pat. Nos. 4,096,227 and 4,985,296, incorporated herein by reference. Suitable particulate fillers may include, for example, inorganic materials such as metals, semi-metals, metal oxides, glass, ceramic and the like. Alternatively, other suitable particulate fillers may include, for example, organic materials selected from activated carbon, carbon black, polymeric resin, graphite and the like. In one preferred embodiment, at least one layer of multilayered porous expanded PTFE tape comprises at least one filler. Preferably, the at least one filler comprises at least one of silica, barium sulfate and glass beads.

Substantially air impermeable layers positioned between the side surfaces of joined tapes prevent fluid from permeating through the gaskets in the radial direction contributing to the low stress to seal nature of the gaskets of the present invention. Substantially air impermeable layers are more air impermeable than the porous expanded PTFE materials used to form the tape. Materials suitable for use in the present invention comprise at least one substantially air impermeable material, or at least one material capable of forming a substantially air impermeable layer having a permeability to air that is less than the porous expanded PTFE of the tape material. Preferred air impermeable materials comprise fluoropolymers, including, but not limited to, tetrafluoroethylene/hexafluoropropylene copolymer (FEP), tetrafluoroethylene/(perfluoroalkyl) vinyl ether copolymer (PFA), PTFE, densified expanded PTFE, and combinations thereof. Preferred are melt processable fluoropolymers. Most preferred are PFA and FEP. In an alternate embodiment, the substantially air impermeable layer may comprise at least one material selected from PFA and FEP, in combination with ePTFE. Air impermeable material may comprise porous PTFE impregnated with fillers such as an elastomer, a fluoroelastomer, a perfluoroelastomer, or a perfluoro silicone elastomer. Where composite tape comprises more than one substantially air impermeable layer, the layers may comprise the same or different air impermeable materials. Preferred are air impermeable layers having a width of about 0.01 mm to 0.5 mm when calculated, for example, by measuring the distance between two tapes that are joined along aligned side surfaces.

The at least one air impermeable layer extends between the side surfaces of the joined tapes to form the composite tape of the present invention. Preferably, at least two tapes are bonded together by the substantially air impermeable layer along tape side surfaces for the entire length of the composite tape. Where at least one of two tapes to be joined comprises, for example, a plurality of laminated layers, the tape side surface is defined by the laminated edge (e.g., FIG. 5, at 55 ) which extends between upper and lower tape layers (FIG. 5, 53 and 54). The at least one substantially air impermeable layer positioned between the adjacent tape side surfaces preferably extends from the upper tape layers to the lower tape layers of the two tapes. Preferably, the air impermeable layer extends substantially completely between the upper and lower tape layers, e.g. generally in the x-z plane of the tape, for the entire length of the composite tape.

Preferred gaskets are formed from composite tape comprising a plurality of multilayered porous multiaxially expanded PTFE tapes having upper and lower laminate tape layers in the x-y plane of the tape. Preferably the upper and lower laminate tape layers define upper and lower gasket surfaces, which are substantially parallel to the sealing surface. Where composite tape comprises monolithic porous ePTFE tape having upper and lower tape surfaces, upper and lower tape surfaces are parallel to the upper and lower gasket surfaces. The x-y plane of expansion of the ePTFE tape layers, or of the monolithic ePTFE, is oriented substantially parallel to upper and lower gasket surfaces of an uncompressed gasket, providing strength in at least both the longitudinal and transverse direction. Preferred composite tapes of the present invention have a substantially uniform thickness across the plurality of joined tapes and substantially air impermeable layer(s). Therefore, uncompressed gaskets formed from the composite tape of the present invention preferably have a uniform thickness across the upper and lower gasket surfaces between inner and outer gasket diameters. As illustrated in FIG. 4, where tape side surfaces are perpendicular to the upper and lower gasket surfaces, the air impermeable layer 62 extends substantially along the x-z plane of the tapes preventing the flow of liquid in the transverse direction through the gasket.

Figure 7:
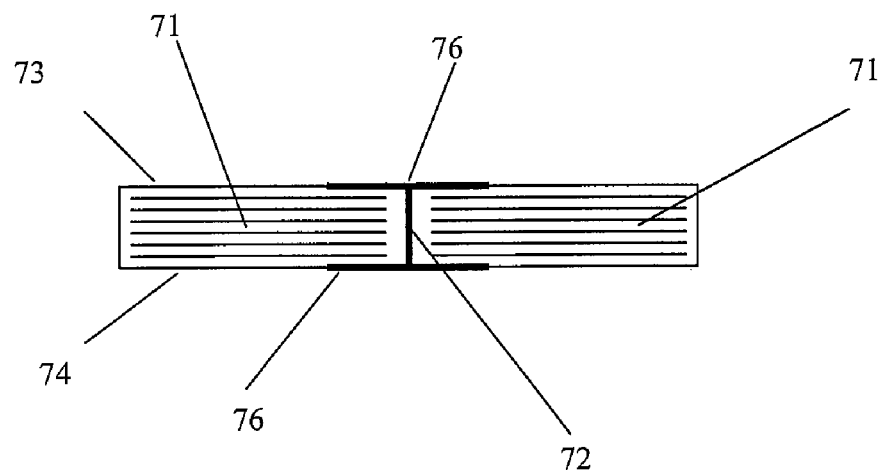
FIG. 7 is a cross-sectional view of a composite low stress to seal tape of the present invention having one barrier layer and upper and lower reinforcing layers.

A variant of the embodiment of FIG. 5 is shown in FIG. 7 as a cross-section of a gasket comprising a composite tape further comprising a reinforcing layer 76 bonded to a portion of upper and lower gasket surfaces 73 and 74. Advantageously, the reinforcing layer provides additional transverse tensile strength to the gasket. Materials suitable for the reinforcing layer include, but are not limited to, PFA, FEP, expanded PTFE, densified expanded PTFE, expanded PTFE fibers, woven expanded PTFE fibers, metal fibers, woven metal fibers or a combination of the above. The reinforcing layer overlaps a portion of at least two of the joined tapes 71 and the substantially air impermeable layer 72. The reinforcing layer is preferably bonded to both the upper and lower gasket surfaces, and may be bonded to a portion of the length of the composite tape or for substantially the entire length of the composite tape. In an alternate embodiment, the reinforcing layer is the same as the at least one substantially air impermeable layer extending between the side surfaces of at least two joined tapes. In this embodiment, the substantially air impermeable layer extends beyond the tape side surfaces and is bonded onto at least one of top and bottom gasket surfaces to form a reinforcing layer. In a further embodiment, the reinforcing layer bonded to top and bottom gasket surfaces comprises at least one substantially air impermeable material, and joins together the at least two tapes which are aligned along side surfaces, but that are not otherwise joined by the substantially air impermeable layers. The reinforcing layer in this embodiment is substantially air impermeable and overlaps the air impermeable layers bonded to the tape side surfaces, and extends the entire length of the composite tape to provide a substantially air impermeable region between two tapes.

FIG. 4 further depicts an adhesive component 67 affixed to the lower gasket surface. One or more adhesive components may be affixed to a composite tape to hold the tape in place while positioning the tape on the sealing surface, for example, in the case of a form-in-place gasket. Preferred are adhesives that are positioned on lower composite tape layers 63 bridging joined tapes and overlapping substantially air impermeable layers 62. Further, preferred adhesives comprise a release layer. Adhesives, such as pressure sensitive adhesives, are suitable for use in the present invention, however, any means known in the art for securing form-in-place-gaskets to the sealing surface may be used in the present invention. Examples of adhesives suitable for use in the present invention may be found in U.S. Pub. No. US2003/0003290 A1, incorporated herein by reference.

The novel composite tape of the present invention having at least two joined porous ePTFE tapes wherein plane of expansion of the ePTFE is parallel the x-y plane of the gasket, and where the two ePTFE tapes aligned along side surfaces separated by a substantially air impermeable layer(s), preferably results from the following novel methods.

In one method of forming a composite tape of the present invention, a process is provided comprising the steps of providing at least two porous ePTFE tapes each having upper and lower tape layers or surfaces, and side surfaces extending between upper and lower tape layers or surfaces, and providing at least one material capable of forming at least one substantially air impermeable layer between the side surfaces of at least two ePTFE tapes. The method further comprises aligning the at least two ePTFE tapes along the tape side surfaces. The at least two tapes are aligned side-by side with upper and lower tape layers or surfaces and the plane of expansion of the ePTFE both in the x-y plane of the tape. The method further comprises joining the at least two ePTFE tapes to form a composite tape which comprises at least two joined ePTFE tapes aligned along side surfaces having at least one substantially air impermeable material extending between the tape side surfaces along the length of the composite tape.

Figure 10:
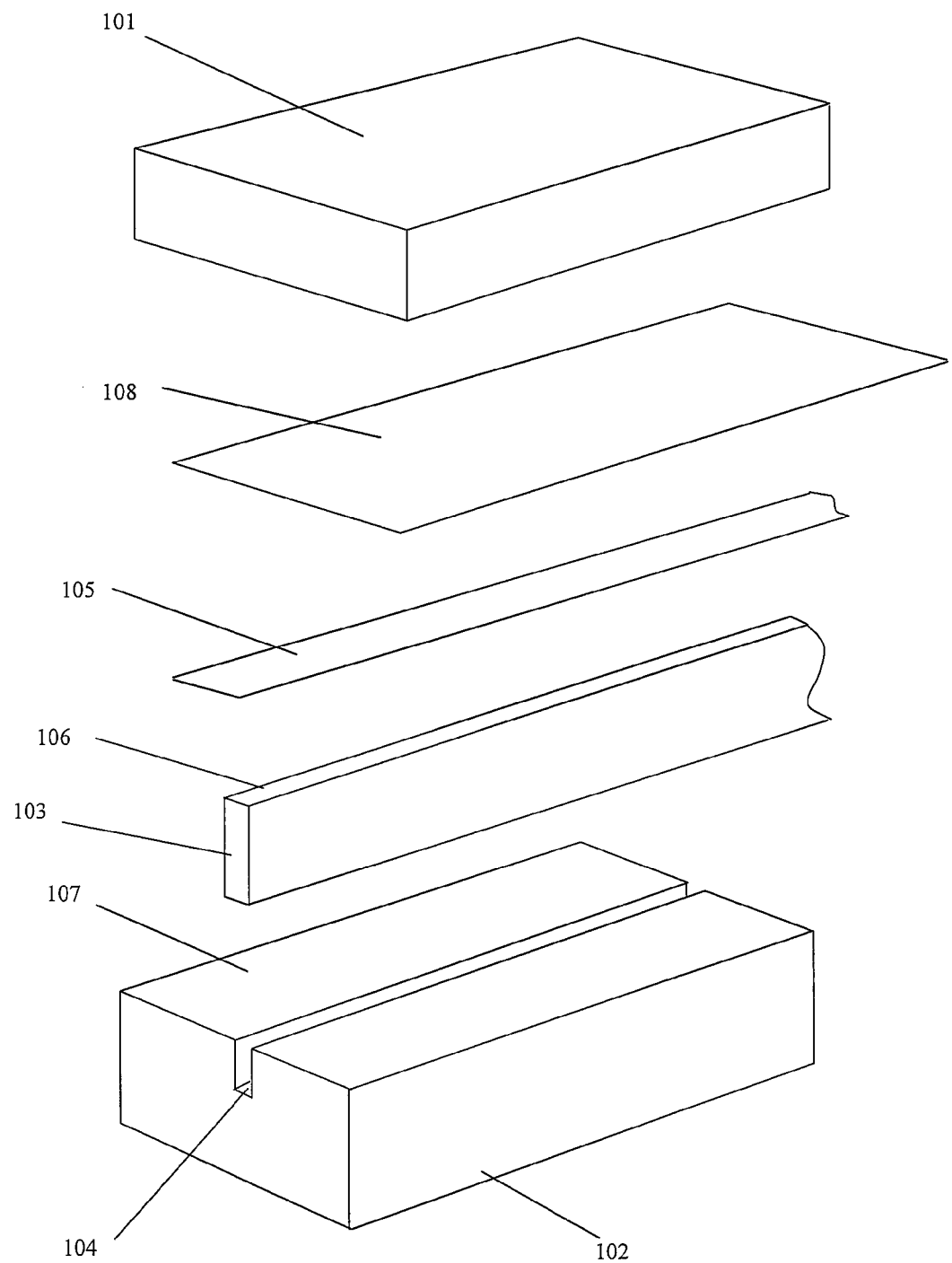
FIG. 10 is an exploded view of a fixture and a method of assembling a tape having a barrier layer.

In a preferred embodiment, a substantially air impermeable layer is first bonded on a side surface of at least one porous PTFE tape prior to aligning and joining at least two ePTFE tapes to form a composite. Preferably, a substantially air impermeable layer is formed on the side surface of both tapes prior to joining the tapes. A method comprises providing a tape having tape side surfaces, and a material capable of forming a substantially air impermeable layer, and aligning the material capable of forming a substantially air impermeable layer along the length of the ePTFE tape on the tape side surface. Heat is provided to the tape and the material capable of forming the substantially air impermeable layer. Sufficient pressure is applied to bond the tape side surface and the material, forming a substantially air impermeable material on the side surface of the tape. A release layer may be provided between the material capable of forming the air impermeable layer and the pressure and/or heat source to prevent sticking. The substantially air impermeable material is bonded to a desired length of the porous ePTFE tape, which is preferably the entire tape length used to form a composite tape. FIG. 10 illustrates a portion of a hot press assembly and a method for welding a substantially air impermeable layer on to the side surface of an ePTFE tape.

Alternately, the material capable of forming a substantially air impermeable layer may, for example, be coated onto the side surface of an ePTFE tape along the length of at least one tape, or at least two tapes, prior to joining the at least two tapes forming the composite tape. Coating may be accomplished by any means, such as spraying, brushing, or powder coating.

Preferably, the step of bonding the at least one material capable of forming an air impermeable layer comprises the steps of contacting, and applying pressure and heat, to the side surface of the porous ePTFE tapes and the at least one material, above the melt temperature of the porous ePTFE and the at least one material, to weld the material and the porous ePTFE together forming a substantially air impermeable layer on the at least one tape side surface. The steps of forming a substantially air impermeable layer on at least one ePTFE tape side surface, including the steps of 1) contacting the ePTFE tapes and the at least one material capable of forming a substantially air impermeable layer, and 2) applying heat and 3) pressure to the materials, may or may be performed simultaneously or sequentially. Further, the steps of forming a substantially air impermeable layer on at least one ePTFE tape side surface may be performed as a step-wise or continuous process along the entire desired length of the tape.

Figure 11A:
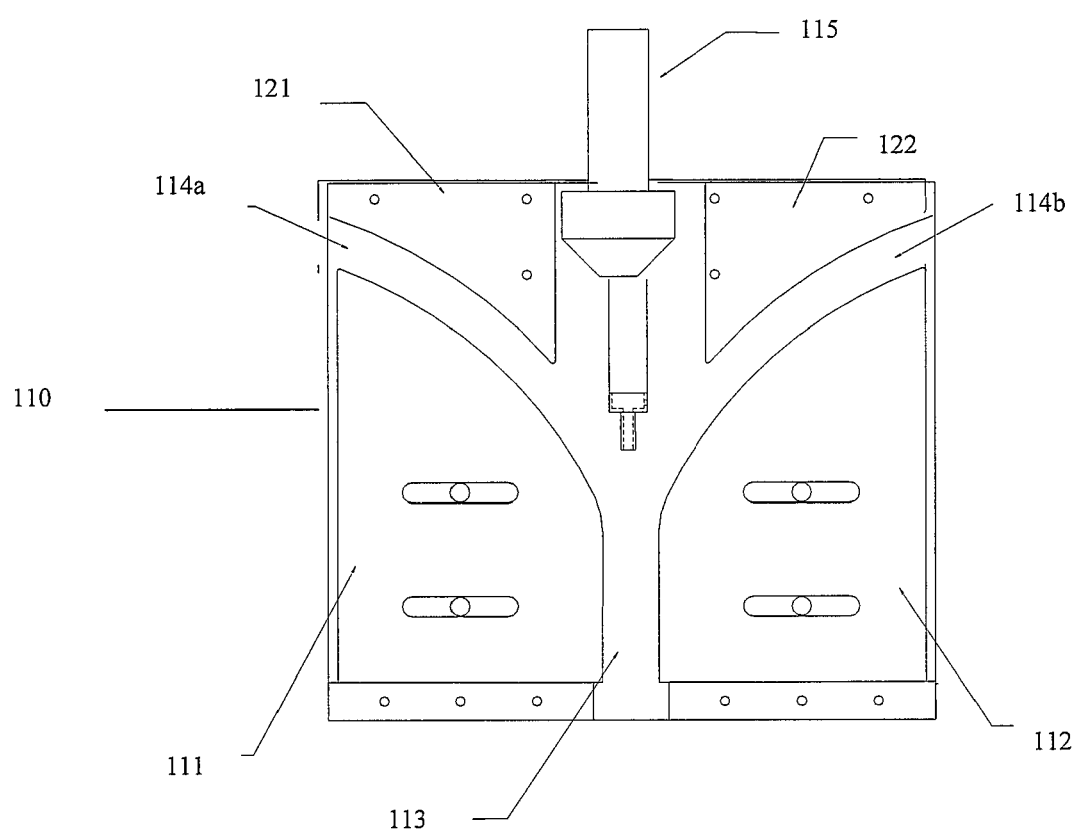
FIG. 11 is a top view of a fixture for assembling a composite tape of the present invention.
Figure 11B:
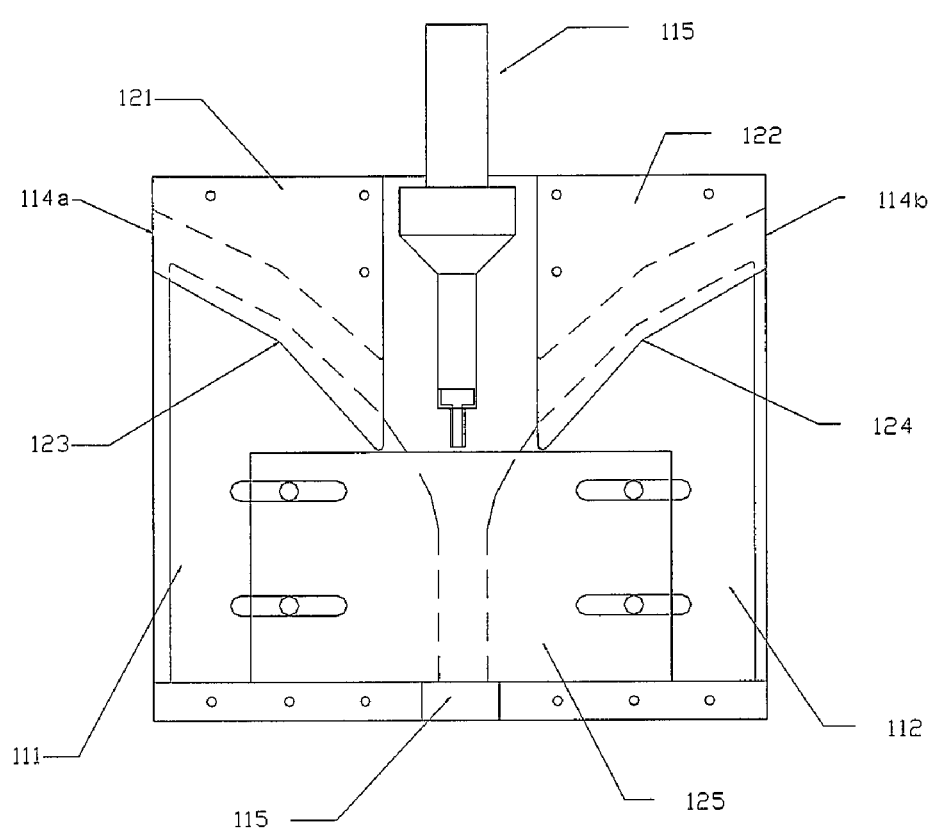

A method for joining at least two porous ePTFE tapes having a substantially air impermeable layer to form a composite preferably comprises the steps of applying heat at a juncture of at least two porous ePTFE tape side surfaces having the substantially air impermeable layer bonded thereto, above the melt temperature of the substantially air impermeable layer, contacting and applying pressure to the at least two heated porous ePTFE tape side surfaces to weld the substantially air impermeable layers of the two porous ePTFE tapes joining the first and second ePTFE tapes to form a tape composite. FIG. 11 illustrates a portion of a welding fixture for welding at least two tapes together to form a composite tape. The steps of joining at least two ePTFE tapes along the laminated side surface, including the steps of 1) applying heat at a juncture of at least two ePTFE tape side surfaces having the substantially air impermeable layer bonded thereto, and 2) contacting and 3) applying pressure to the heated ePTFE side surfaces to weld, may be performed simultaneously or sequentially. Further, the steps of joining at least two ePTFE tapes along the tape side surfaces may be performed step-wise or as a continuous process until the desired length of composite tape is formed.

Figure 11C:
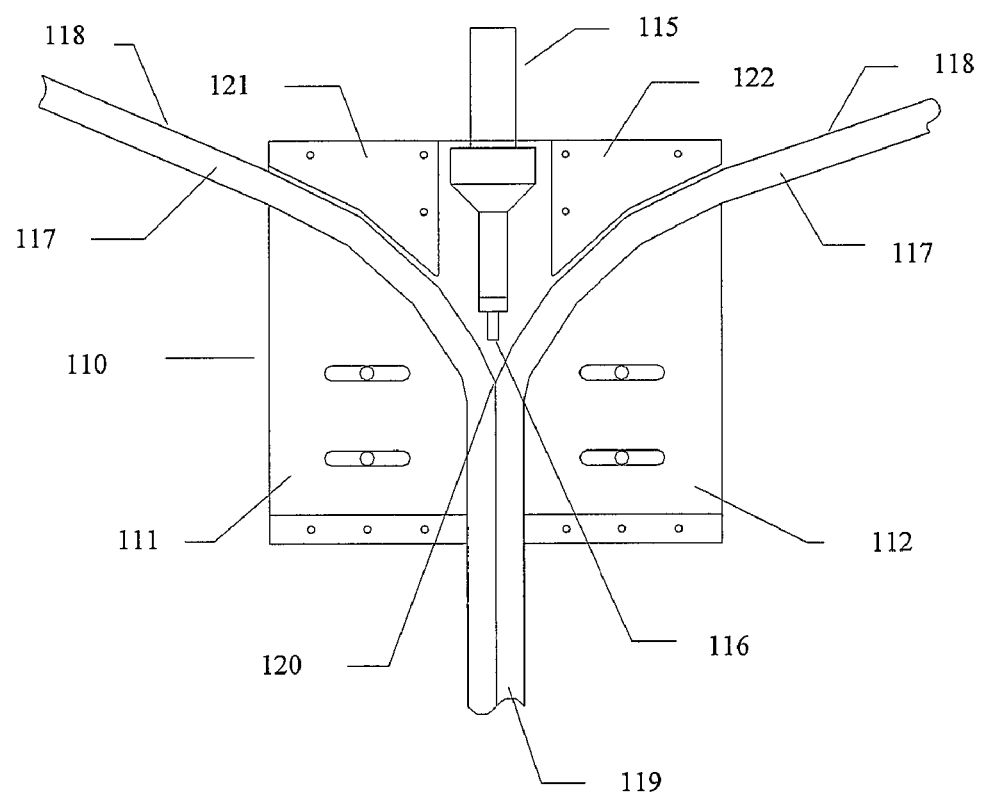

In another embodiment, the steps of forming a substantially air impermeable layer on at least one ePTFE side surface and the steps of joining at least two ePTFE tapes are combined in one continuous process to form a composite tape of any desired length.

Where the method for joining at least two ePTFE tapes along tape side surfaces comprises a heating step, the method includes applying heat directly at the juncture of the at least two tapes (e.g., FIG. 11c at 120). Applying heat directly to the juncture of the at least two tapes advantageously minimizes the transfer of heat throughout the ePTFE tape. Where ePTFE is heated throughout the material to elevated temperatures (above 100° C.), ePTFE shrinks in a direction opposite the direction the PTFE was originally expanded. Thus, where expanded PTFE joined by means of heat fusion using an oven or heated platens wherein the ePTFE is heated throughout the material, ePTFE tends to shrink unless ePTFE is restrained in the length and width directions (x and y directions), for example, by means of applying pressure on the ePTFE in the z direction. However, at the temperatures required to heat fuse ePTFE together (typically greater than 250° C.), ePTFE becomes softer and more compressible. The pressure required in the z direction at such temperatures to prevent shrinkage in the x and y directions would result in significant compression of the ePTFE in the thickness direction thus densifying the ePTFE into a hard, rigid mass unsuitable for use in the present invention. Thus, the present invention advantageously provides a method for welding two ePTFE tapes together to provide a composite tape while maintaining the sealability properties inherent in ePTFE. Further, in preferred methods for preparing gaskets and composite tapes of the present invention, the density of ePTFE does not increase by more than about 30%, preferably more than about 20% and further preferred by more than about 10% as a result of heat and pressure applied during the steps of joining the at least two tapes.

Figure 12:
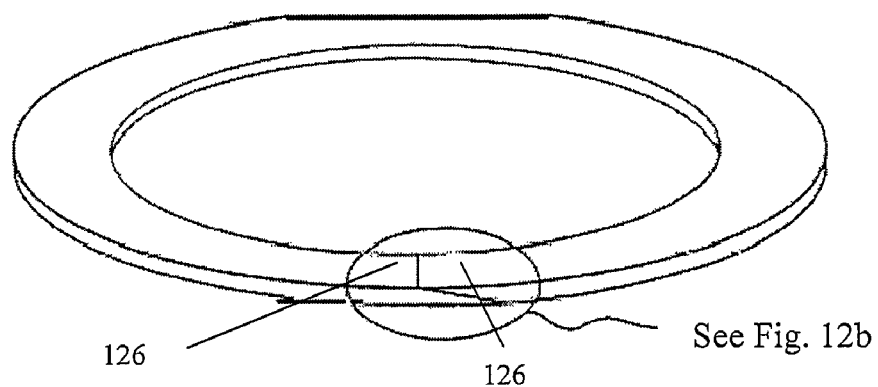
FIG. 12 is a three-quarter perspective view of a form-in-place gasket and a method for joining two ends of a tape of the present invention.
Figure 12:
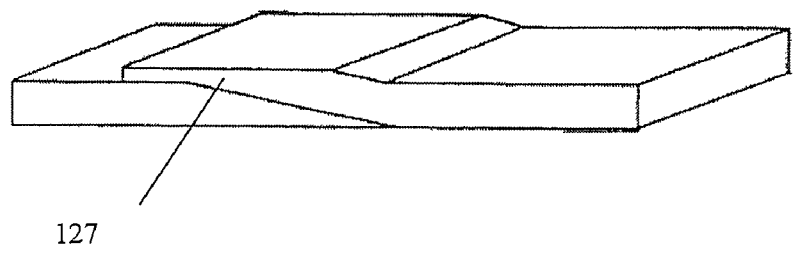

Gaskets or seals, such as form-in-place gaskets (FIG. 12a), may be formed in virtually any dimension of importance to sealing applications. Gaskets are formed from composite tape of the present invention by joining one tape at the longitudinal tape beginning and end. Gaskets are also formed from multiple composite tapes of the present invention by joining the composite tapes lengthwise at the longitudinal ends of more than one composite tape. The tape ends may be joined by any method known in the art for joining tape material. A preferred method for joining tape ends comprises the method of skiving described, for example, in commonly owned U.S. Pat. No. 5,964,465 to Mills et al. As shown in FIG. 12a and b longitudinal ends 126 of the composite tape are skive cut 127 in diagonal fashion and joined with each other in such a way that the sealing surface is covered entirely and there is no significant increase in gasket thickness due to joining the two ends of the composite tape. Alternatively, a seal between longitudinal ends of a composite tape to form a gasket may be formed by any technique, such as overlapping, or the like, which creates an effective seal.

Methods for forming composite tapes of the present invention may further comprise the steps of bonding a reinforcing layer to at least one of the upper and lower tape or gasket surfaces, and preferably both upper and lower tape or gasket surfaces. Preferred methods comprise bridging the at least two tapes and the substantially air impermeable layer located between the two joined tapes with a reinforcing layer, and bonding the reinforcing layer thereto. The reinforcing layer may be bonded along a portion of the length of a tape, or a portion of a gasket circumference, such as at the skive or joint of the longitudinal end, or to substantially the entire gasket or tape length. Alternately, a method for forming composite tapes of the present invention comprise the step of joining at least two tapes by bonding a reinforcing layer to upper and lower tape surfaces along the entire length of the composite tape.

EXAMPLES

Example 1

An ePTFE/FEP composite form-in-place gasket of the present invention was produced in the following manner.

A length of GORE-TEX® Series 600 Gasket Tape (ePTFE tape) having a nominal width of approximately 20 mm (0.79 inches) and a nominal thickness of approximately 6 mm (0.25 inches) was obtained from W.L. Gore & Associates, Inc. of Newark, Del. The GORE-TEX® Series 600 Gasket Tape is comprised of a plurality of a biaxially expanded PTFE layers laminated in the z-axis having tensile strength in the longitudinal (x-axis) and transverse (y-axis) directions as taught in U.S. Pat. No. 5,964,465 to Mills et al.

A Teflon® FEP Film, Type A having a width of approximately 13 mm (0.5 inches) and a thickess of approximately 0.025 mm (0.001 inches), was obtained from E.I. du Pont de Nemours, Inc. of Wilmington, Del.

The FEP film was melt bonded to one side surface of the ePTFE tape along the length (x-z plane) using a hot press substantially similar to the press shown in FIG. 10 with the upper press platen 101 heated to about 375° C. and the lower press platen 102 kept at ambient temperature. The upper and lower platens 101 and 102 had a length of approximately 200 mm (8 inches). Therefore, 200 mm sections of the ePTFE tape 103 were coated with the FEP 105 at a time. The ePTFE tape 103 was placed in a channel 104 in the lower platen with the side surface 106 of the ePTFE tape extending approximately 0.25 mm to 0.5 mm above the top surface 107 of the lower platen. The FEP film 105 was placed on the side surface 106 of the ePTFE tape and centered. Kapton® polyimide film 108 was obtained from E.I. du Pont de Nemours, Inc. of Wilmington, Del. A piece of the Kapton® film 108 was placed on top of the FEP film 104 as a release layer to prevent the FEP from sticking to the heated upper platen 101. The upper platen 101 was lowered with sufficient pressure being applied so that the upper platen was in contact with the lower platen 102. The upper platen was held in place for approximately five seconds and then lifted from the lower platen. The Kapton® film 108 was removed from the formed ePTFE/FEP composite tape. The ePTFE/FEP composite tape was removed from the channel in the lower platen and the next 200 mm section was inserted and the lamination process was repeated. After the entire length of ePTFE tape was coated on one side surface with the FEP film, the excess FEP film was trimmed from the ePTFE/FEP composite tape using a razor blade. Two lengths of the ePTFE/FEP composite tape were produced according to this method.

Two ePTFE/FEP composite tapes 117 having a width of approximately 19.5 mm were welded together along the two side surfaces of the tapes that had been coated with the FEP film 118 using a welding fixture 120 substantially similar to the fixture shown in FIG. 11. The left compression plate 111 and right compression plate 112 were positioned to form an exit channel 113 having a width of approximately 32 mm wide. The 32 mm width in the exit channel allowed for about 20% compression of the tapes in the width direction, providing contact between the two FEP coated edges 118 of the ePTFE/FEP composite tapes necessary for a strong welded joint. The two tapes were loaded into the welding fixture between left and right guide plates 121 and 122 and left and right compression plates 111 and 112 through left and right tape inlets 114a and b. A Leister® Hot Jet S air gun 115 (Leister Process Technologies, Sarnen, Switzerland) was positioned at the interface 116 of the adjoining edges of the FEP-coated tape at a distance of approximately 15 mm from the juncture 120 of the two tapes and was set to a temperature setting of 6 (maximum) and an air flow setting of 4 (maximum). After the hot air reached a temperature of approximately 450° C. as measured at the exit point of the hot air gun nozzle, the ePTFE/FEP composite tapes were manually pulled through the fixture at the exit channel 113 at a rate of approximately 100 mm/minute (4 inches/minute) until the entire length of the two composite tapes were welded together. The exit channel 113 was covered by an exit channel cover plate 125. The welded composite tape 119 was then trimmed to a final width of about 20 mm using a razor knife, keeping the FEP layer centered in the tape.

The final width of the welded tape was about 20.8 mm (0.817 inches) and the final thickness was about 5.7 mm (0.224 inches). A double-sided pressure sensitive adhesive having a width of about 10 mm was applied to one surface of the welded tape along the length of the tape and centered between the two edges. The pressure sensitive adhesive was a styrene butadiene rubber (SBR) based adhesive with a polyester carrier film having a release paper on one side.

The welded tape made according to this example was formed into a gasket and tested for sealability in accordance with the procedures of the Sealability Test. The results can be found in FIG. 14.

Example 2

An ePTFE/FEP composite form-in-place gasket of the present invention was produced substantially according to the method described in Example 1. The welded tape was trimmed to a final width of about 20.4 mm (0.803 inches) with the FEP layer centered between the two side edges of the welded tape, and the final thickness was about 5.6 mm (0.221 inches). A double-sided pressure sensitive adhesive having a width of about 10 mm was applied to one surface of the tape along the length of the tape and centered between the two edges of the welded tape. The pressure sensitive adhesive was a styrene butadiene rubber (SBR) based adhesive with a polyester carrier film and with a release paper on one side.

The welded tape made according to this example was formed into a gasket and tested for sealability in accordance with the procedures of the Sealability Test. The results can be found in FIG. 14.

Example 3

An ePTFE/FEP composite form-in-place gasket of the present invention was produced substantially according to the method described in Example 1. The welded tape was trimmed to a final width of about 20.8 mm (0.817 inches) with the FEP layer centered between the two side edges of the welded tape, and the final thickness was about 5.6 mm (0.222 inches). A double-sided pressure sensitive adhesive having a width of about 10 mm was applied to one surface of the welded tape along the length of the tape and centered between the two side edges. The pressure sensitive adhesive was a styrene butadiene rubber (SBR) based adhesive with a polyester carrier film and with a release paper on one side. The welded tape made according to this example was formed into a gasket and tested for sealability in accordance with the procedures of the Sealability Test. The results can be found in FIG. 14.

Example 4

An ePTFE/FEP composite form-in-place gasket of the present invention was produced having top and bottom reinforcing layers comprising FEP in the following manner.

A welded ePTFE/FEP tape was produced substantially according to the method described in Example 1. The welded tape was trimmed to a final width of about 20 mm keeping the FEP layer centered between the two side edges of the welded tape. FEP films were then applied to top and bottom surfaces of the welded ePTFE/FEP composite tape using the hot press shown in FIG. 10. The upper platen 101 of the hot press 100 was set to about 375° C. The lower platen 102 was kept at ambient temperature. The bottom surface of the welded tape was placed on the top surface 107 of the lower platen. A 13 mm (0.5 inch) wide FEP film (Teflon® FEP film, Type A E.I.

du Pont de Nemours, Inc., Wilmington, Del.) with a thickness of about 0.025 mm (0.001 inches) was placed on the top surface of the welded composite tape and centered on the FEP weld seam of the composite tape. A layer of Kapton® polyimide film was placed on top of the FEP film to act as a release layer to prevent the FEP film from sticking to the heated upper platen. The upper platen 101 was lowered on to the welded tape with a light pressure being applied. The upper platen was held in place for approximately five (5) seconds to allow the FEP to melt and bond to the ePTFE. After about a five (5) second dwell the upper platen was lifted from the welded ePTFE/FEP composite tape and the Kapton® film was removed from the tape. This process was repeated until the entire length of the welded ePTFE/FEP composite tape was coated on the top surface with the 13 mm wide FEP film. This process was then repeated to apply the 13 mm wide FEP film to the bottom surface of the welded composite tape.

The final width of the welded ePTFE/FEP tape having top and bottom FEP layers was about 20.8 mm (0.819 inches) and the final thickness was about 5.5 mm (0.218 inches). A double-sided pressure sensitive adhesive having a width of about 10 mm was applied to one surface of the tape along the length of the tape and centered between the two side edges. The pressure sensitive adhesive was a styrene butadiene rubber (SBR) based adhesive with a polyester carrier film having with a release paper on one side.

The welded tape made according to this example was formed into a gasket and tested for sealability in accordance with the procedures of the Sealability Test. The results can be found in FIG. 14.

Comparative Example 5

Figure 2:
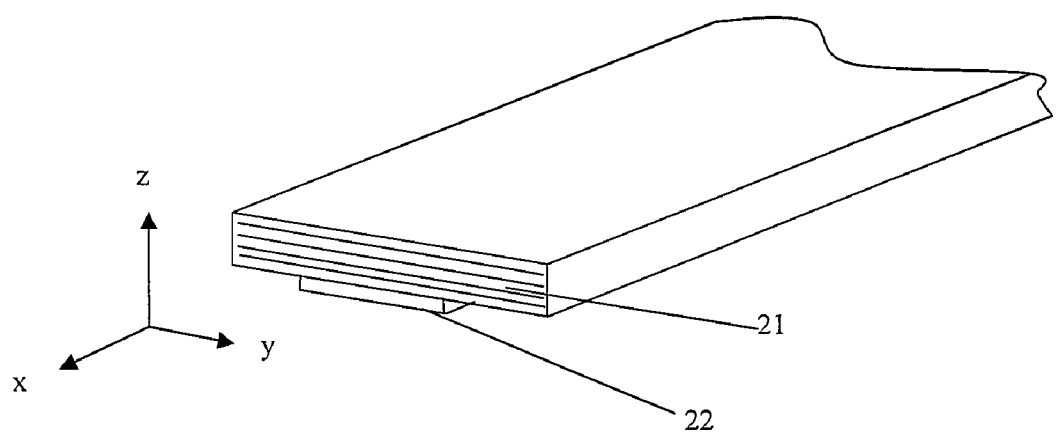
FIG. 2 is a three-quarter perspective view of a conventional multilayer gasketing tape comprising an adhesive layer.

A sample of GORE-TEX® Series 600 Gasket Tape as represented by FIGS. 2 was obtained from W.L. Gore & Associates, Inc. of Newark, Del. The tape was comprised of a multiple layers of ePTFE membrane 21 having a nominal thickness of 6 mm and a nominal width of 20 mm and length of approximately 1000 mm. A double-sided pressure sensitive adhesive 22 having a width of about 10 mm was applied to one surface of the tape along the length of the tape and centered between the two edges. The pressure sensitive adhesive was a styrene butadiene rubber (SBR) based adhesive with a polyester carrier film and with a release paper on one side.

The tape was formed into a gasket and tested for sealability in accordance with the procedures of the Sealability Test. The results can be found in FIG. 14.

Comparative Example 6

Figure 3:
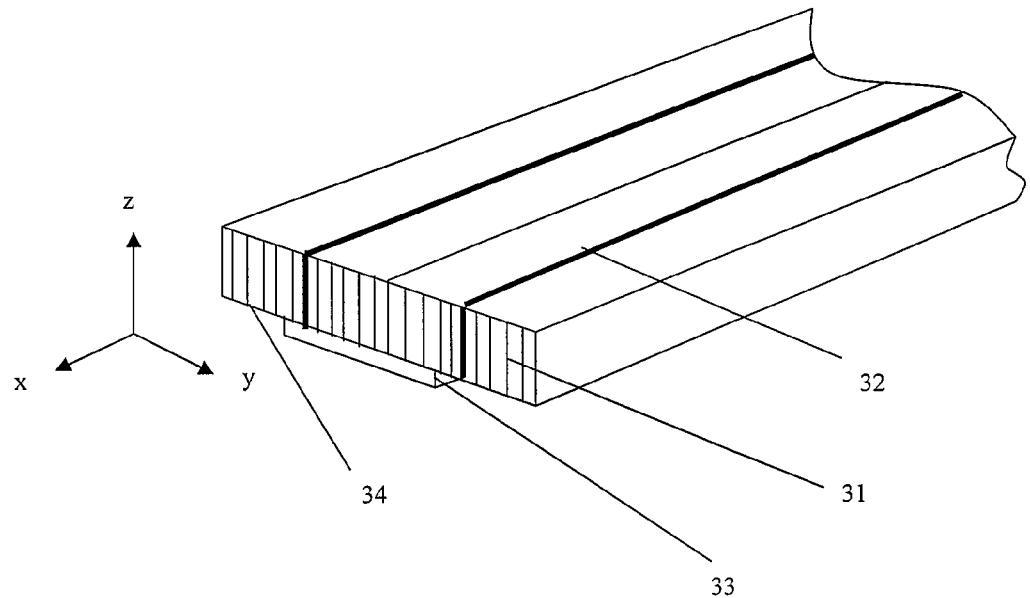
FIG. 3 is a three-quarter perspective view of a multilayer joined type of sealing tape having an adhesive layer.

A 20 mm wide and 6 mm thick tape was produced as represented by FIG. 3. Two flat multilayered ePTFE sheets 31 each with a laminated thickness of about 10 mm and each comprising a 50 μm thick compact ePTFE fluid penetration-preventing layer 32 interposed therein, were laminated together producing a flat sheet with a laminated height of approximately 20 mm. The flat sheet was slit to a width corresponding to the gasket thickness of approximately 6 mm. A double-sided adhesive tape 33 (#9458 by Sumitomo 3M, Japan) 2 μm thick and 10 mm wide was applied in about the center on one of the laminated end faces 34 along the length of the tape. The resulting tape having a laminated height (corresponding to the width of the tape) of 20 mm and a laminated strip width (corresponding to the thickness of the tape) of 6 mm in which the ePTFE film layers were oriented perpendicular to the x-y plane of the tape. Therefore, the plane of expansion of the ePTFE was oriented perpendicularly to the x-y plane of the tape and the sealing surface.

The tape made according to this example was formed into a gasket and tested for sealability in accordance with the procedures of the Sealability Test. The results can be found in FIG. 14.

Example 7

A form-in-place gasket of the present invention was produced substantially according to the process described in Example 1.

A length of Gore-Tex® Series 600 Gasket Tape (ePTFE tape) having a nominal width and thickness of 25 mm (1 inch) and 6 mm (0.25 inches), respectively, was obtained from W.L. Gore & Associates, Inc. of Newark, Del. A length of GORE-TEX® Series 600 Tape having a nominal width and thickness of 13 mm (0.5 inches) and 6 mm (0.25 inches), respectively, was obtained from W.L. Gore & Associates, Inc. of Newark, Del.

The ePTFE tape having a width of 25mm was laminated along the length on one side surface substantially according to the method described in Example 1 with a 13 mm wide, 0.025 mm thick FEP film described in Example 1, to form 25 mm wide ePTFE/FEP tape.

The 13 mm wide ePTFE tape was laminated on both side surfaces of the length with the FEP film following the procedures described in Example 1. First one side surface was laminated with the FEP film along the entire length of the ePTFE tape. The excess FEP was then trimmed from the ePTFE tape. The opposite side surface of the ePTFE tape was then laminated with the FEP film along the entire length and the excess FEP trimmed to form 13mm wide ePTFE/FEP tape.

The 25 mm wide ePTFE/FEP tape was cut widthwise forming two equal lengths of 25 mm wide ePTFE/FEP tape. One length of 25 mm wide ePTFE/FEP tape was welded to one side surface of the 13 mm wide ePTFE/FEP tape following the procedures describe in Example 1, joining the FEP coated edges of both tapes. The second length of 25 mm wide ePTFE/FEP tape was then welded to the other side surface of the 13 mm ePTFE/FEP portion of the previously welded 13 mm and 25 mm wide ePTFE/FEP tapes forming a tape comprising three ePTFE sections each separated by FEP layers.

The final width of the welded tape was about 55.7 mm (2.191 inches) and the final thickness was approximately 5.9 mm (0.232 inches). A double-sided pressure sensitive adhesive having a width of about 25 mm was applied to one surface of the tape along the length of the tape and centered between the two edges overlaying the FEP layers. The pressure sensitive adhesive was a styrene butadiene rubber (SBR) based adhesive with a polyester carrier film and with a release paper on one side.

Tape made according to the procedure of this example was formed into a gasket and tested for leakage in accordance of the procedure for Leakage Test and the results can be seen in Table 1.

Example 8

An ePTFE/FEP composite form-in-place gasket having top and bottom FEP reinforcing layers was produced.

The gasket was produced substantially according to the method described in Example 4 with the exception that the initial width of the ePTFE tape was approximately 30 mm (1.18 inches) and the top and bottom FEP reinforcing layers were each comprised of a 25 mm (1 inch) wide and 0.025 mm (0.001 inch) thick FEP film obtained from E.I. du Pont de Nemours, Inc. of Wilmington, Del.

The final width of the welded tape was 55 mm (2.164 inches) and the thickness was nominally 6 mm (0.25 inches). A double-sided pressure sensitive adhesive having a width of about 25 mm was applied to one surface of the tape along the length of the tape and centered between the two edges. The pressure sensitive adhesive was a styrene butadiene rubber (SBR) based adhesive with a polyester carrier film and with a release paper on one side.

The welded tape made according to this example was formed into a gasket and tested for leakage substantially in accordance with the procedures of the Leakage Test with the exception that the final retightening of the clamps on the glass lined steel fixture was only to 50 Nm generating a line force of only 90 N/mm instead of the 111 Nm torque to reestablish the 200 N/mm line force on the gasket. The results can be seen in Table 1.

Comparative Example 9

A sample of GORE-TEX® Series 600 Gasket Tape as represented by FIG. 2 was obtained from W.L. Gore & Associates, Inc. of Newark, Del. having a nominal thickness of 6 mm and a nominal width of 55 mm and length of approximately 1800 mm. A double-sided pressure sensitive adhesive having a width of about 25 mm was applied to one surface of the tape along the length of the tape and centered between the two edges. The pressure sensitive adhesive was a styrene butadiene rubber (SBR) based adhesive with a polyester carrier film and with a release paper on one side.

The tape was formed into a gasket and tested for leakage in accordance with the procedures of the Leakage Test. The results can be found in Table 1.

Comparative Example 10

A 55 mm wide and 6 mm thick tape was produced. Six flat ePTFE sheets each with a laminated thickness of about 10 mm and each having a 50 μm thick compact ePTFE fluid penetration-preventing layer interposed therein were laminated together producing a flat sheet with a laminated height of approximately 55 mm. The flat sheet was slit to a width corresponding to the thickness of the gasket of approximately 6 mm. A double-sided adhesive tape (#9458 by Sumitomo 3M, Japan) 2 μm thick and 25 mm wide was applied in about the center on one of the laminated end faces along the length of the tape. The resulting tape having a laminated height (corresponding to the width of the tape) of 55 mm and a laminated strip width (corresponding to the thickness of the tape) of 6 mm in which the ePTFE film layers were oriented perpendicular to the x-y plane of the tape. Therefore, the plane of expansion of the ePTFE was oriented perpendicularly to the x-y plane of the tape and the sealing surface.

The tape sample was formed into a gasket and tested in accordance with the procedures of the Leakage Test. The results can be seen in Table 1.

TABLE 1

| | | | Leakage Test Results | | |
|---|---|---|---|---|---|
| | Width | Thickness | Leakage Measurements (mg/m/s) | | |
| Sample ID | (mm) | (mm) | 1 | 2 | 3 |
| Example 7 | 55.7 | 5.9 | 0.0293 | Gross Leakage | 0.0173 |
| Example 8 | 55 | 6 | n/a | Gross Leakage | 0.0238 |
| Comparative Example 9 | 55 | 6.0 | 0.28 | Gross Leakage | 0.11 |
| Comparative Example 10 | 55 | 6.0 | 2.41 | Gross Leakage | 1.25 |

Example 11

An ePTFE/FEP composite form-in-place gasket of the present invention was produced substantially according to the method described in Example 1 with the exception that the initial width of the ePTFE tape was approximately 30 mm (1.18 inches) and FEP film thickness was approximately 0.05 mm.

The final width of the welded tape was 53 mm (2.08 inches) and the thickness was nominally 6.2 mm (0.245 inches). The welded tape was cut into sections having a length of approximately 25 mm. The 25 mm long samples were tested according to the Tensile Strength Test Procedure described herein and the results can be seen in Table 2 and FIG. 16.

Comparative Example 12

A sample of GORE-TEX® Gasket Tape (uniaxially expanded PTFE tape) was obtained from W.L. Gore & Associates, Inc. of Newark, Del. having a thickness of approximately 3.2 mm and a width of 200 mm and length of approximately 300 mm. Tensile test specimens were cut from this sample of GORE-TEX® Gasket Tape having a width of approximately 25 mm and a length of approximately 55 mm. The length of the tensile test specimen was oriented in the transverse direction (along the y axis) of the GORE-TEX® Gasket Tape. The specimens were tested according to the Tensile Strength Test Procedure described herein and the results can be seen in Table 2 and FIG. 16.

Comparative Example 13

An ePTFE tape with compact ePTFE fluid penetration-preventing layers was made substantially in accordance with the procedures of Comparative Example 10 with the exception that the double-sided adhesive was not applied to the tape. Three 25 mm long sections were cut from the 55 mm wide tape. The 25 mm long specimens were tested in the Tensile Strength Test. The results can be seen Table 2 and FIG. 16.

TABLE 2

Tensile Test Specimen Data and Results

| | Sample # | Width (in.) | Width (mm) | Thickness (in.) | Thickness (mm) | Maximum Tensile Load (lbs.) | Maximum Tensile Load (kgf) | Tensile Strength (psi) | Tensile Strength (MPa) |
|---|---|---|---|---|---|---|---|---|---|
| Example 11 | 1 | 0.984 | 25.0 | 0.252 | 6.4 | 164 | 74 | 660 | 4.55 |
| | 2 | 0.988 | 25.1 | 0.250 | 6.4 | 148 | 67 | 599 | 4.13 |
| | 3 | 0.990 | 25.1 | 0.249 | 6.3 | 146 | 66 | 593 | 4.09 |
| Comparative Example 12 | 1 | 0.987 | 25.1 | 0.133 | 3.4 | 38 | 17 | 290 | 2.00 |
| | 2 | 0.984 | 25.0 | 0.132 | 3.4 | 39 | 18 | 301 | 2.08 |
| | 3 | 0.990 | 25.1 | 0.132 | 3.4 | 37 | 17 | 282 | 1.94 |
| Comparative Example 13 | 1 | 1.044 | 26.5 | 0.247 | 6.3 | 20 | 9 | 77 | 0.53 |
| | 2 | 1.023 | 26.0 | 0.247 | 6.3 | 27 | 12 | 105 | 0.72 |
| | 3 | 1.021 | 25.9 | 0.247 | 6.3 | 39 | 18 | 153 | 1.06 |

TEST METHODS AND PROCEDURES

Sealability Test Procedures

Figure 13:
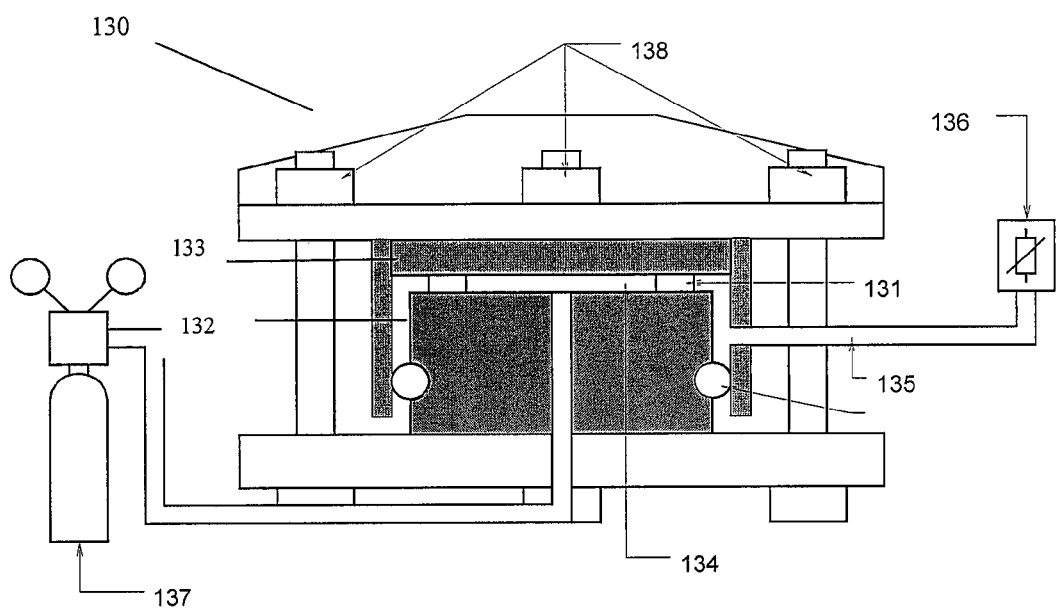
FIG. 13 is a side cross-sectional view of a test apparatus used to measure sealability of gaskets.

The sealability of gaskets made substantially according to Examples 1-4 and Comparative Examples 5-6 was determined by measuring leak rates using a computer controlled, hydraulically driven 130 test fixture, as seen in FIG. 13. Tape samples were formed into gaskets 131 and installed in the test fixture and using the skive-cut overlapping technique taught in U.S. Pat. No. 5,964,465 to Mills et al. as follows.

The first end of the tape samples were skive cut on a diagonal with a skive length of about 25 mm. The release paper was removed from the adhesive layer on the tape samples. The adhesive layer held the tapes in position as the tape was being formed to a circular shape. The tapes were formed to a gasket having an inner diameter of about 220 mm on the lower platen 133 of the test fixture. The trailing end of the tape was positioned on top of the skive cut on the leading end of the tape. The second skive cut was made on the trailing end of the tape so that a smooth transition was created at the overlap of the leading and trailing ends of the tape.

The gasket samples were compressed by hydraulic press 138 between the upper and lower platens 132 and 133 to a stress of about 6 MPa. The internal pressure in the high pressure zone 134 was increased to about 27 bar using nitrogen gas as supplied by the compressed air bottle 137 as the test fluid. The internal pressure was maintained in the high pressure zone throughout the test period. As the nitrogen gas leaked past the gasket sample, the pressure in the low pressure zone 135 increased. The change in pressure in the low pressure zone was monitored by the pressure differential switch 136. The leak rate was calculated by the test fixture's software program based on the change in pressure in the low-pressure zone after a 90 minute (5400 second) dwell time and based on the following equation:

$$LR = (\rho_{nitrogen} \times V_o \times \Delta P)/(d \times \Pi \times \Delta t \times p_{atm})$$

where:
LR=leak rate (mg/m×sec)
$\rho_{nitrogen}$=density of nitrogen at ambient conditions (mg/cm$^3$)
$V_o$=volume within test flange (cm$^3$)
d=average gasket diameter (m, meters)
　d=(outer diameter+inner diameter)/2
ΔP=change in internal pressure in the low pressure zone=$P_o$−Pf
　$P_o$=initial internal pressure at t=0 seconds (bar)
　$P_f$=final pressure at t=Δt (bar)
Δt=test time (seconds)
$p_{atm}$=atmospheric pressure (bar)

Figure 14:
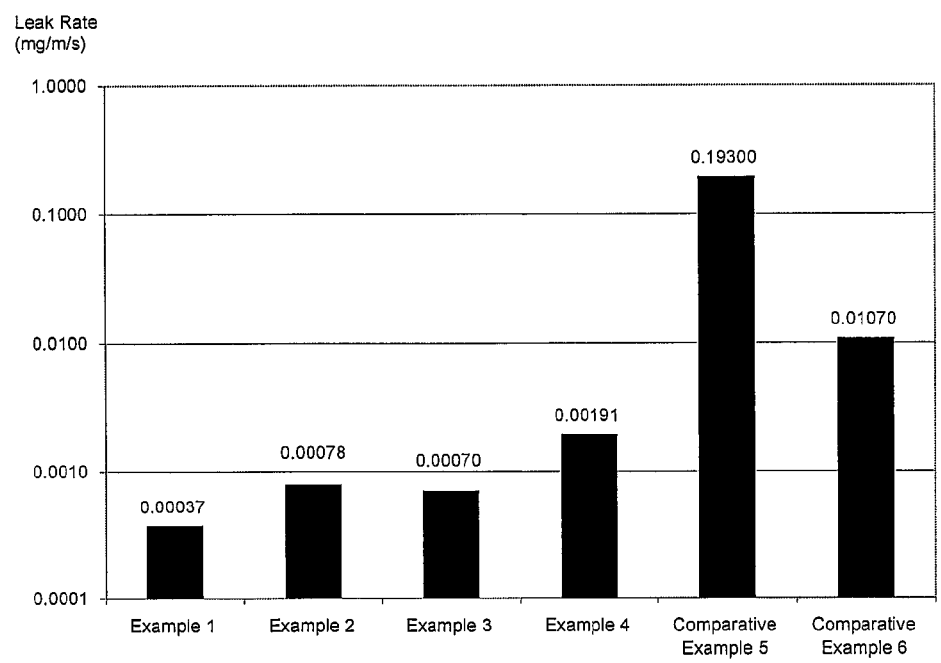
FIG. 14 is a graphical representation of leak rate results of gaskets at a gasket stress of about 6 MPa.

The leak rates for each example tested can be seen in FIG. 14. The graph shows that all of the inventive examples tested, Examples 1 through 4, had significantly lower leak rates than the comparative examples. A decrease in leak rate of at least about two orders of magnitude was realized with the inventive examples having an impermeable layer as compared with Comparative Example 5 which is an ePTFE tape without any impermeable layers interposed therein. As compared with Comparative Example 6 which had fluid penetration preventing layers comprising densified ePTFE, a reduction in leak rate of at least about one order of magnitude was realized with the inventive examples, Examples 1 through 4. The reduction in leak rate with the inventive examples is attributable in part to the incorporation of the substantially air impermeable layer(s) in the gasket and to the substantially parallel orientation of the plane of expansion of the expanded PTFE with the flange surface.

Leakage Test Procedures: Glass Lined Steel Test Fixture

The leakage behavior of gaskets made substantially according to Examples 7 and 8, and Comparative Examples 9 and 10 were tested on an actual glass lined steel flange through a thermal cycle. The inner and outer diameters of the glass lined steel flanges were approximately 430 mm and 520 mm, respectively. Test gaskets were installed on the lower flange using the skive cut overlapping technique taught in U.S. Pat. No. 5,964,465 to Mills et al. The first end of the tape samples were skive cut on a diagonal with a skive length of about 50 mm. The release paper was removed from the adhesive on the tape samples. The adhesive layer held the tapes in position as the tape was being formed around the lower flange. The trailing end of the tape was positioned on top of the skive cut on the leading end of the tape. The second skive cut was made on the trailing end of the tape so that a smooth transition was created at the overlap of the leading and trailing ends of the tape. The upper flange was positioned on top of the gasket and aligned with the lower flange. The flanges were bolted together using twelve M24 clamps. The clamps were tightened to a torque of 111 N-m generating a line force load on the gasket of approximately 200N/mm. The line force is equal to the total force on the gasket supplied by the tightening of the clamps divided by the average circumference of the gasket. The average circumference is determined by multiplying the average diameter of the gasket [(gasket outside diameter+gasket inside diameter)/2] by pi. Ten minutes after the initial torque, the clamps were retightened to 111 N-m. The internal pressure was then increased to 6 bar using compressed air. After a 24 hour dwell under pressure at ambient temperature, the first leakage measurement was recorded. The fixture was then loaded in to an oven and re-pressurized to 6 bar with compressed air. The temperature of the oven was set to 200° C. for a period of 16 hours. After cooling to room temperature, the second leakage measurement was recorded. The clamps were then retightened to 111 N-m to reestablish the 200 N/mm line force on the gasket. The fixture was re-pressurized to 6 bar with compressed air. The third and final leakage measurement was then taken. The leak rates were determined based on the change in internal pressure in the test fixture as measured by a differential pressure switch according to the following equation:

$$LR = (\rho_{air} \times V_o \times \Delta P)/(d \times \Pi \times \Delta t \times p_{atm})$$

where:
LR=leak rate (mg/m×sec)
$\rho_{nitrogen}$=density of air at ambient conditions (mg/cm³)
$V_o$=volume within test flange (cm³)
d=average gasket diameter (m, meters)
    d=(outer diameter+inner diameter)/2
ΔP=change in internal pressure=$P_o$–Pf
    $P_o$=initial internal pressure at t=0 seconds (bar)
    $P_f$=final pressure at t=Δt (bar)
Δt=test time (seconds)
$p_{atm}$=atmospheric pressure (bar)

The leak rates measured for each example can be seen in Table 1. The results in Table 1 show that after the 24 hour dwell at room temperature the inventive example (Example 7) had significantly lower leak rate as compared with Comparative Examples 9 and 10. After the 16 hour dwell at 200° C., all of the gaskets experienced gross leakage (pressure change too large to be measured by the differential pressure switch). After the re-tightening of the clamps back to the 111 N-m torque (with the exception of Example 8 in which the clamps were re-tightened to only 50 N-m), the inventive examples again had significantly less leakage than the comparative examples.

Figure 15:
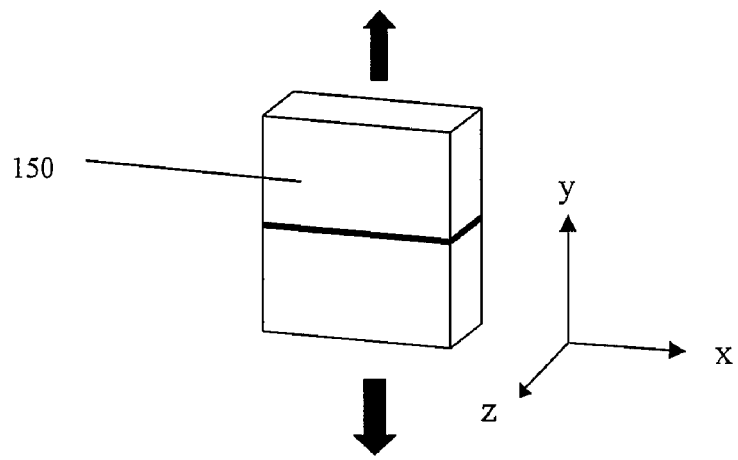
FIG. 15 illustrates the orientation of test specimens during the Tensile Test Procedure.

Tensile Strength Test Procedures:

The tensile strength of gaskets of Example 11, Comparative Example 12 and Comparative Example 13 was determined by performing a tensile test on the samples in accordance with procedures outlined in ASTM D638-00 and ASTM F152-95 test procedures. As illustrated in FIG. 15 for Example 11 the samples 150 were tested in the transverse or "y" direction of the tapes. The specimens were tested using an Instron test machine (model number 5567) with a 10 kN load cell. The extension rate was set at 2 inches/minute (50 mm/minute) and the initial jaw separation was set to 1 inch (25 mm). The arrows in FIG. 15 indicate the direction of the tensile force applied to the samples. The Instron test machine automatically recorded the load in pounds (lbs.) and extension data in inches. The load data was converted to a tensile stress using the following equation:

stress=load (lbs.)/initial cross sectional area (in²)

where initial cross sectional area (in²)=initial width (in.)=initial thickness (in.)

From the test data the tensile strength was determined by dividing the maximum load achieved during the test by the initial cross sectional area of the specimen.

Tensile Strength (psi)=maximum load (lbs.)/cross sectional area (in²)

For the welded and laminated samples the tensile strength equals the bond strength of the weld or lamination if the samples broke at the welded or laminated interface.

Figure 16:
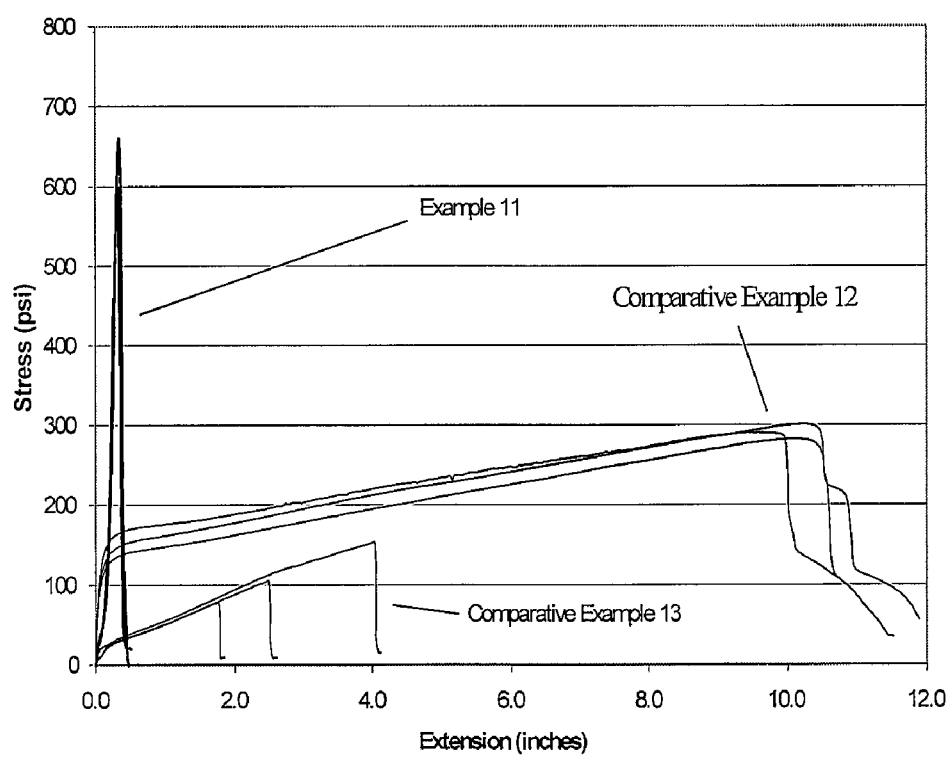
FIG. 16 is a graphical representation of Tensile Strength Test results.

The Tensile Test sample data and test results can be found in Table 2 and FIG. 16. The results illustrated in FIG. 16 show that the bond strength of the welded joint in the inventive example, Example 11, is about four times stronger than the bond strength in the laminated layers of Comparative Example 13. The results demonstrate that gasket material formed from ePTFE film layers laminated in the width direction of the gasket (perpendicular to the x-y plane of the gasket), as was the case with Comparative Example 13, have significantly reduced tensile strength in the width direction compared to the inventive materials. Furthermore, higher tensile strength was achieved in uniaxially expanded PTFE material (no transverse expansion), Comparative Example 12, than in the laminated ePTFE material where the lamination is in the width direction (y direction) as in Comparative Example 13.

Furthermore, as illustrated in FIG. 16, the amount of extension in the inventive material of Example 11 at the maximum stress was only about 0.5 inches as compared with the 2 to 10 inches of extension in the comparative examples. This indicates that gasket materials of the present invention, when compressed between flanges, will be less likely to cold flow.

These results further demonstrate that the preferred orientation of the plane of expansion of the expanded PTFE is parallel to the x-y plane of the gasket material (and parallel to the flange surface).

Wide-Angle X-ray Scattering Measurements

The plane of expansion of a multiaxially expanded PTFE gasket tape material was verified with wide-angle X-ray scattering measurements.

Samples of gasket tape material were cut from a length of GORE-TEX® Series 300 Gasket Tape with a nominal thickness of 3 mm. The GORE-TEX® Series 300 Gasket Tape material is comprised of multiple layers of a biaxially expanded PTFE membrane laminated together in the thickness direction. The ePTFE membrane layers are expanded in the longitudinal (x-direction) and transverse (y-direction) directions with the thickness oriented with the z-direction. Therefore, the plane of expansion is the x-y plane of the membrane and the Gasket Tape.

Figure 18:
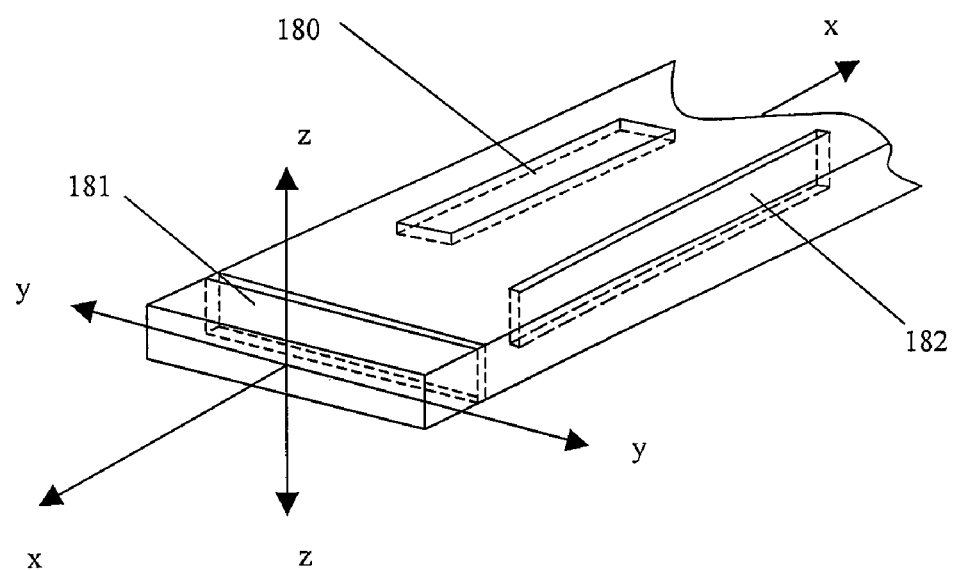
FIG. 18 is a three-quarter perspective view of a gasket tape and orientation.

As illustrated in FIG. 18 test samples were cut parallel to the x-y plane (170), y-z plane (171) and the x-z plane (172) from the GORE-TEX Series 300 Gasket Tape. Four rectangular samples were cut using an LMI Laser Cutter from each planar orientation to approximately 3 mm by 15 mm by 0.5 mm. For the samples cut from the x-y plane (170), membrane layers were removed from a section of the nominally 3 mm thick tape to produce a tape section with a nominal thickness of 0.5 mm. From this 0.5 mm thick section, the rectangular test samples were cut to a width and length of about 3 mm and 15 mm, respectively, with the sample width parallel to the Gasket Tape width (y-direction) and the sample length parallel to the Gasket Tape length (x-direction). In these samples, the plane defined by the sample length and width (x-y plane) is parallel to the membrane layers and the plane of expansion of the ePTFE.

For the test samples cut in the x-z plane (172), two parallel cuts, approximately 0.5 mm apart, were made in the x-direction of the 3 mm thick Gasket Tape material. From this 0.5 mm wide and 3 mm thick section the 15 mm long test samples were cut. For these samples, the 3 mm by 15 mm area defined the x-z plane.

For the test samples cut in the y-z plane (171), two parallel cuts, approximately 0.5 mm apart, were made in the y-direction of the 3 mm thick Gasket Tape material. From this 0.5 mm wide and 3 mm thick section the 15 mm long test samples were cut. For these samples, the 3 mm by 15 mm area defined the y-z plane.

All measurements were made in transmission mode using a Rigaku R-Axis IV Image Plate X-ray Analyzer mounted on a Rigaku Ultra 18 kW rotating anode x-ray generator with a graphite monochromator and a 0.3 mm pinhole collimator. Operating conditions on the generator for all experiments were 50 kcV and 200 mA. Radiation type was Cu $K_\alpha$. Sample-to-detector distance was set at approximately 120 mm, and calibrated using a silicon powder standard. All measurements were made on a temperature-controlled stage maintained at approximately 24±1° C. Two-dimensional image data was processed using Rigaku R-Axis image processing software to obtain I vs. 2θ scans. The scans were collected by radial integration over the angular range from 2θ~0° to 2θ~55° in increments of Δ2θ=0.044°.

The I vs. 2θ scans were processed using Jade 6.1 XRD Pattern Processing & Identification software purchased from Materials Data, Inc. The data processing procedure was as follows. Scans and associated air scattering background files were read into the software and scaled to match maximum intensity counts in the range of 2θ=6°-8°. The air scattering file was then used to define the scattering background and subtracted from the I vs. 2θ scans obtained from the samples. Finally, the position and intensity of the primary scattering peaks were identified using the software's standard peak search routine. It should be noted that the data was originally collected in two-dimensional form, and was analyzed without any correction into a form that would be directly analogous to data collected with a linear detector.

Figure 17:
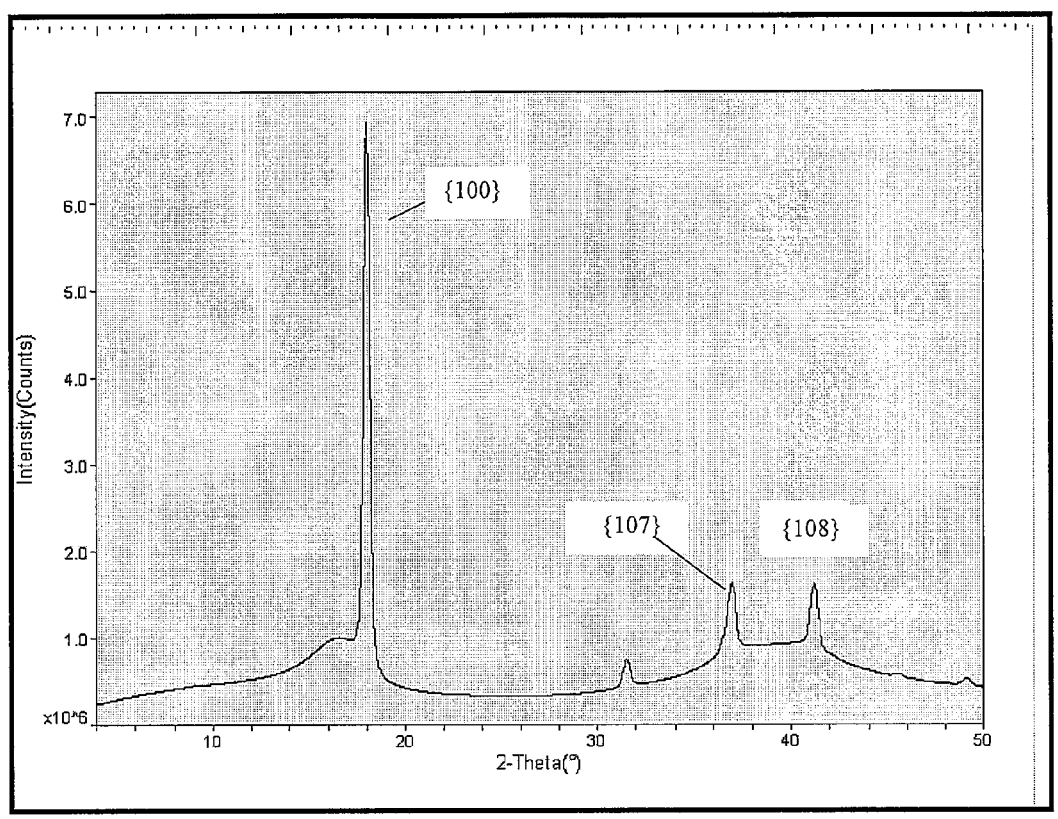
FIG. 17 is a graphical representation of Wide-Angle X-ray Scattering Test results.

A typical I vs. 2θ diffraction scan is shown in FIG. 17. All scans show the characteristic diffraction peaks of polytetrafluoroethylene. The strongest peak, occurring near 2θ=18.1°, is attributable to the {100} crystalline planes. The next most intense diffraction peaks occur near 2θ=37.10° and 2θ=41.4°, and are attributed to the {107} and {108} crystalline planes, respectively (see Eduard S. Clark, "Unit Cell Information on Some Important Polymers," Chapter 30, *Physical Properties of Polymers Handbook*, James E. Mark, Ed. New York,: American Institute of Physics, 1996).

The GORE-TEX® Series 300 Gasket Tape material is comprised of multiple layers of a biaxially expanded PTFE membrane laminated together in the thickness direction. Orientation, or texture, is developed in the PTFE within the membrane during expansion that is retained within the Gasket Tape. Due to this texture, the relative intensity of the {100} and {108} peaks in diffraction scans obtained from the samples of the Gasket Tape is a function of the physical orientation of the sample relative to the thickness direction of the Gasket Tape.

When Gasket Tape samples are measured with the x-ray beam incident on the sample face in a direction that is perpendicular to the plane of expansion (x-y plane), the intensity of the {108} peak relative to the intensity of {100} peak is higher than for samples measured in other orientations. For example, in the case where the samples were cut parallel to x-y plane and measured with the x-ray beam perpendicular to the x-y plane (parallel to the z direction), the I vs. 2θ diffraction scans show higher relative {108} peak intensities than scans from samples cut in the x-z and y-z planes and measured with the x-ray beam perpendicular to those faces (parallel to the y direction, and parallel to the x direction, respectively). This is illustrated in Table 3, in which data are presented from the analysis of I vs. 2θ diffraction scans for twelve (12) samples, four (4) cut from three (3) different orientations relative to the thickness direction of the Gasket Tape. In Table 3, the relative {108} peak intensity is reported as a percentage of the {100} peak intensity, to normalize for sample-to-sample variation in thickness, density, or measurement time. As illustrated in Fig, 18 and noted in Table 3, samples with x-z orientation were measured such that the x-ray beam was incident on the x-z face in a direction parallel to the y-direction. Similarly, samples with y-z orientation were measured such that the x-ray beam was incident on the y-z face in a direction parallel to the x-direction, and samples with x-y orientation were measured such that the x-ray beam was incident on the x-y face in a direction parallel to the z direction. Samples were cut and positioned such that the x-ray beam was incident on the 3 mm by 15 mm face.

TABLE 3

| Sample | Plane | Beam Direction | {108} Peak Intensity (% of {100} Peak) |
|---|---|---|---|
| 1 | x-y | parallel to z | 35.7 |
| 4 | x-y | parallel to z | 32.5 |
| 7 | x-y | parallel to z | 32.9 |
| 12 | x-y | parallel to z | 33.3 |
| 2 | y-z | parallel to x | 6.2 |
| 6 | y-z | parallel to x | 6.5 |
| 9 | y-z | parallel to x | 6.1 |
| 10 | y-z | parallel to x | 5.7 |
| 3 | x-z | parallel to y | 13.5 |
| 5 | x-z | parallel to y | 12.2 |
| 8 | x-z | parallel to y | 12.1 |
| 11 | x-z | parallel to y | 13.2 |

In Table 3, the {108} relative peak intensity, expressed as a percentage of the corresponding {100} peak intensity within a single I vs. 2θ x-ray scan, is the variety of gasket sections. Samples 1, 4, 7, and 12 which were measured in the x-y orientation with the x-ray beam parallel to the z direction have significantly higher relative {108} diffraction intensities than the samples measured in the x-z orientation or in the y-z orientation with the x-ray beam directed as stated above. Thus, the highest {108} relative peak intensity is measured for samples positioned such that the x-ray beam is incident on the sample in a direction 1 perpendicular to the plane of expansion of the biaxially expanded PTFE membrane layers. Therefore, comparison of {108} relative peak intensities in different orientations can be used to identify the plane of expansion of ePTFE in a Gasket Tape.

I claim:

1. A method of forming a composite tape comprising the steps of:
 a. providing at least two porous expanded polytetrafluoroethylene (ePTFE) tapes, the tapes having a plurality of ePTFE layers, upper and lower layers, and side surfaces extending between upper and lower layers,
 b. providing at least one material capable of forming a substantially air impermeable layer,
 c. bonding the at least one material on at least one side surface of each of the at least two ePTFE tapes to form a substantially air impermeable layer comprising the steps of
  contacting and applying pressure and heat to the ePTFE tape and the at least one material above the melt temperature of the ePTFE and the at least one material, to weld the material and the ePTFE together forming a substantially air impermeable layer on the tape side surface, and
 d. joining at least two ePTFE tapes along side surfaces comprising the steps of 1. applying heat at a juncture of at least two ePTFE tape side surfaces having the substantially air impermeable layer bonded thereto, above the melt temperature of the substantially air impermeable layer, and
2. contacting and applying pressure to the at least two heated ePTFE tapes to weld the substantially air impermeable layers of the at least two ePTFE tapes joining the tapes to form a tape composite.

2. The method of claim 1, comprising bonding at least one substantially air impermeable material to at least one of the tape side surfaces along the entire tape length prior to joining at least two ePTFE tapes.

3. The method of claim 1, further comprising coating at least one side surface of at least one ePTFE tape along the entire length with the material capable of forming at least one substantially air impermeable layer prior to joining at least two ePTFE tapes.

4. The method of claim 1 wherein the density of the ePFE tape does not increase more than 30% after joining the at least two ePTFE tapes.

5. The method of claim 1 wherein the density of the ePFE tape does not increase more than 20% after joining the at least two ePTFE tapes.

6. The method of claim 1 wherein the density of the ePFE tape does not increase more than 10% after joining the at least two ePTFE tapes.

7. The method of claim 1, further comprising joining two ends of the composite tape to form a gasket.

8. The method of claim 7, wherein upper and lower tape surfaces correspond to upper and lower gasket surfaces.

9. The method of claim 8, wherein the gasket is uncompressed and has a substantially uniform thickness across the upper and lower gasket surfaces.

10. The method of claim 1, wherein the at least one material capable of forming a substantially air impermeable material comprises at least one fluoropolymer.

11. The method of claim 10, wherein the fluoropolymer is a melt processable fluoropolymer.

12. The method of claim 11, wherein the fluoropolymer comprises tetrafluoroethylene/ perfluoroalkyl vinyl ether copolymer (PFA).

13. The method of claim 11, wherein the fluoropolymer comprises tetrafluoroethylene/ hexafluoropropylene copolymer (FEP).

14. The method of claim 11, wherein the fluoropolymer comprises polytetrafluoro ethylene (PTFE).

15. The method of claim 11, wherein the fluoropolymer comprises densified expanded polytetrafluoroethylene.

16. The method of claim 1, wherein the at least one material capable of forming a substantially air impermeable material extends substantially completely between upper and lower tape surfaces.

17. The method of claim 1, wherein the at least one material capable of forming a substantially air impermeable layer has a permeability to air less than the expanded polytetrafluoroethylene (ePTFE)).

18. The method of claim 1, further comprising the step of bonding a reinforcing layer to at least one of the upper and lower tape surfaces bridging the adjoining side surfaces.

19. The method of claim 1, further comprising the step of bonding a reinforcing layer to upper and lower tape surfaces bridging the at least two tapes along the entire length of the tape.

20. The method of claim 1, wherein the step of joining at least two tapes comprises bonding a reinforcing layer to upper and lower tape surfaces along the entire length of the tape.

21. The method of claim 1, wherein the steps of contacting, applying heat and pressure to form a substantially air impermeable layer on at least one ePTFE tape side surface are continuous.

22. The method of claim 1 wherein the steps of applying heat, contacting and applying pressure to join at least two ePTFE tapes along side surfaces are continuous.

23. The method of claim 1, wherein the steps of forming a substantially air impermeable layer on at least one ePTFE side surface and the steps of joining at least two ePTFE tapes along side surfaces are continuous.

24. The method of claim 1, wherein the ePTFE tapes comprise a filler.

25. A method of forming a composite tape comprising the steps of:
    a. providing at least two laminate porous expanded polytetrafluoroethylene (ePTFE) tapes having a plurality of ePTFE layers, the tapes having upper and lower laminate layers, and side surfaces extending between upper and lower laminate layers
    b. providing at least one material capable of forming a substantially air impermeable layer comprising at least one of FEP and PFA
    c. bonding the at least one material on at least one side surface of the at least two ePTFE tapes to form a substantially air impermeable layer comprising the steps of contacting and applying pressure and heat to the ePTFE tapes and the at least one material above the melt temperature of the ePTFE and the at least one material to weld the material and the ePTFE together forming a substantially air impermeable layer on the at least one tape side surface, and
    d. joining at least two ePTFE tapes along side surfaces comprising the steps of:
        1. applying heat at a juncture of at least two ePTFE tape side surfaces having the substantially air impermeable layer bonded thereto, above the melt temperature of the substantially air impermeable layer, and
        2. contacting and applying pressure to the at least two heated ePTFE tapes to weld the substantially air impermeable layers of the at least two ePTFE tapes joining the tapes to form a tape composite.

* * * * *

UNITED STATES PATENT AND TRADEMARK OFFICE
CERTIFICATE OF CORRECTION

PATENT NO.        : 7,943,003 B2
APPLICATION NO.   : 11/620397
DATED             : May 17, 2011
INVENTOR(S)       : Kevin E. Dove It is certified that error appears in the above-identified patent and that said Letters Patent is hereby corrected as shown below:

IN THE SPECIFICATIONS:
In column 4, line 48: change "comprise" to --comprises--
In column 5, line 27: remove the first occurrence of "the"
In column 6, line 44: change "techique" to --technique--
In column 9, last line: change "otherwisejoined" to --otherwise joined--
In column 11, line 22: remove "may or"
In column 12, line 51: change "comprise" to --comprises--
In column 15, line 25: change "having" to --and--
In column 15, line 36: remove "a"
In column 16, line 39: change "describe" to --described--
In column 18, line 66: insert --in-- before "Table 2"
In column 19, line 28: change "were" to --was--
In column 19, line 63: the "f" should be subscript as in line 65
In column 21, line 18: the "f" should be subscript as in line 20
In column 23, line 36: change "37.10" to --37.1--
In column 24, line 33: insert --given for-- before "the"

IN THE CLAIMS:
In column 25, claim 4: change "ePFE" to --ePTFE--
In column 25, claim 5: change "ePFE" to --ePTFE--
In column 25, claim 6: change "ePFE" to --ePTFE--
In column 25, claim 14: change "polytetrafluoro ethylene" to --polytetrafluoroethylene--

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

PATENT NO.         : 7,943,003 B2
APPLICATION NO.    : 11/620397
DATED              : May 17, 2011
INVENTOR(S)        : Kevin E. Dove It is certified that error appears in the above-identified patent and that said Letters Patent is hereby corrected as shown below:

IN THE SPECIFICATIONS:
In column 4, line 48: change "comprise" to --comprises--
In column 5, line 27: remove the first occurrence of "the"
In column 6, line 44: change "techique" to --technique--
In column 9, last line: change "otherwisejoined" to --otherwise joined--
In column 11, line 22: remove "may or"
In column 12, line 51: change "comprise" to --comprises--
In column 15, line 25: change "having" to --and--
In column 15, line 36: remove "a"
In column 16, line 39: change "describe" to --described--
In column 18, line 66: insert --in-- before "Table 2"
In column 19, line 28: change "were" to --was--
In column 19, line 63: the "f" should be subscript as in line 65
In column 21, line 18: the "f" should be subscript as in line 20
In column 23, line 36: change "37.10" to --37.1--
In column 24, line 33: insert --given for-- before "the"

IN THE CLAIMS:
Column 25, line 17 (Claim 4, line 1): change "ePFE" to --ePTFE--
Column 25, line 20 (Claim 5, line 1): change "ePFE" to --ePTFE--
Column 25, line 23 (Claim 6, line 1): change "ePFE" to --ePTFE--
Column 25, line 45 (Claim 14, line 2): change "polytetrafluoro ethylene" to --polytetrafluoroethylene--

This certificate supersedes the Certificate of Correction issued August 9, 2011.

Signed and Sealed this
Thirtieth Day of August, 2011

David J. Kappos
*Director of the United States Patent and Trademark Office*

Page 1 of 1